United States Patent
Pradeep et al.

(10) Patent No.: US 9,336,535 B2
(45) Date of Patent: May 10, 2016

(54) NEURO-RESPONSE DATA SYNCHRONIZATION

(71) Applicants: Anantha K. Pradeep, Berkeley, CA (US); Robert T. Knight, Berkeley, CA (US); Ramachandran Gurumoorthy, Berkeley, CA (US)

(72) Inventors: Anantha K. Pradeep, Berkeley, CA (US); Robert T. Knight, Berkeley, CA (US); Ramachandran Gurumoorthy, Berkeley, CA (US)

(73) Assignee: The Nielsen Company (US), LLC, New York, NY (US)

( * ) Notice: Subject to any disclaimer, the term of this patent is extended or adjusted under 35 U.S.C. 154(b) by 0 days.

(21) Appl. No.: 14/177,698

(22) Filed: Feb. 11, 2014

(65) Prior Publication Data

US 2014/0164095 A1    Jun. 12, 2014

Related U.S. Application Data

(63) Continuation of application No. 12/778,828, filed on May 12, 2010, now Pat. No. 8,655,428.

(51) Int. Cl.
| | | |
|---|---|---|
| *A61B 5/04* | (2006.01) | |
| *G06Q 30/02* | (2012.01) | |
| *A61B 5/0476* | (2006.01) | |
| *A61B 5/00* | (2006.01) | |
| *A61B 5/0408* | (2006.01) | |

(Continued)

(52) U.S. Cl.
CPC .......... *G06Q 30/0242* (2013.01); *A61B 5/0476* (2013.01); *A61B 5/6814* (2013.01); *A61B 5/0006* (2013.01); *A61B 5/04085* (2013.01); *A61B 5/0488* (2013.01); *A61B 5/0496* (2013.01)

(58) Field of Classification Search
None
See application file for complete search history.

(56) References Cited

U.S. PATENT DOCUMENTS

| | | |
|---|---|---|
| 2,549,836 A | 4/1951 | McIntyre et al. |
| 3,490,439 A | 1/1970 | Rolston |
| 3,572,322 A | 3/1971 | Wade |

(Continued)

FOREIGN PATENT DOCUMENTS

| | | |
|---|---|---|
| GB | 1374658 | 11/1974 |
| GB | 2221759 | 2/1990 |

(Continued)

OTHER PUBLICATIONS

Office Action, issued by the United States Patent and Trademark Office in connection with U.S. Appl. No. 13/730,511, on Jan. 30, 2014, 6 pages.

(Continued)

*Primary Examiner* — Etsub Berhanu
(74) *Attorney, Agent, or Firm* — Hanley, Flight & Zimmerman, LLC

(57) ABSTRACT

An example system includes a headset to gather first data comprising first neuro-response data and second neuro-response data from a user while the user is exposed to stimulus material. In the example system, the headset comprises a first sensor to gather the first neuro-response data, the first neuro-response data comprising at least one of electroencephalographic data or magnetoencephalographic data, and a second sensor to gather the second neuro-response data, the second neuro-response data comprising facial emotion encoding data. The headset also comprises a processor to synchronize the first neuro-response data, the second neuro-response data and the stimulus material to generate synchronized data and determine an effectiveness of a portion of the stimulus material based on the synchronized data.

25 Claims, 8 Drawing Sheets

(51) Int. Cl.
   *A61B 5/0488* (2006.01)
   *A61B 5/0496* (2006.01)

(56) References Cited

U.S. PATENT DOCUMENTS

| | | | |
|---|---|---|---|
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,075,657 A | 2/1978 | Weinblatt |
| 4,145,122 A | 3/1979 | Rinard et al. |
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,626,904 A | 12/1986 | Lurie |
| 4,632,122 A | 12/1986 | Johansson et al. |
| 4,683,892 A | 8/1987 | Johansson et al. |
| 4,686,999 A | 8/1987 | Snyder et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,885,687 A | 12/1989 | Carey |
| 4,894,777 A | 1/1990 | Negishi et al. |
| 4,913,160 A | 4/1990 | John |
| 4,955,388 A | 9/1990 | Silberstein |
| 4,967,038 A | 10/1990 | Gevins et al. |
| 4,973,149 A | 11/1990 | Hutchinson |
| 4,987,903 A | 1/1991 | Keppel et al. |
| 5,003,986 A | 4/1991 | Finitzo et al. |
| 5,010,891 A | 4/1991 | Chamoun |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy |
| 5,137,027 A | 8/1992 | Rosenfeld |
| 5,213,338 A | 5/1993 | Brotz |
| 5,226,177 A | 7/1993 | Nickerson |
| 5,243,517 A | 9/1993 | Schmidt et al. |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,331,544 A | 7/1994 | Lu et al. |
| 5,339,826 A | 8/1994 | Schmidt et al. |
| 5,345,281 A | 9/1994 | Taboada et al. |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,410,609 A | 4/1995 | Kado et al. |
| 5,447,166 A | 9/1995 | Gevins |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,537,618 A | 7/1996 | Boulton et al. |
| 5,550,928 A | 8/1996 | Lu et al. |
| 5,617,855 A | 4/1997 | Waletzky et al. |
| 5,655,534 A | 8/1997 | Ilmoniemi |
| 5,676,138 A | 10/1997 | Zawilinski |
| 5,687,322 A | 11/1997 | Deaton et al. |
| 5,720,619 A | 2/1998 | Fisslinger |
| 5,724,987 A | 3/1998 | Gevins et al. |
| 5,729,205 A | 3/1998 | Kwon |
| 5,736,986 A | 4/1998 | Sever, Jr. |
| 5,740,035 A | 4/1998 | Cohen et al. |
| 5,762,611 A | 6/1998 | Lewis et al. |
| 5,771,897 A | 6/1998 | Zufrin |
| 5,774,591 A | 6/1998 | Black et al. |
| 5,787,187 A | 7/1998 | Bouchard et al. |
| 5,800,351 A | 9/1998 | Mann |
| 5,802,208 A | 9/1998 | Podilchuk et al. |
| 5,802,220 A | 9/1998 | Black et al. |
| 5,812,642 A | 9/1998 | Leroy |
| 5,817,029 A | 10/1998 | Gevins et al. |
| 5,848,399 A | 12/1998 | Burke |
| 5,892,566 A | 4/1999 | Bullwinkel |
| 5,945,863 A | 8/1999 | Coy |
| 5,961,332 A | 10/1999 | Joao |
| 5,983,129 A | 11/1999 | Cowan et al. |
| 5,995,868 A | 11/1999 | Dorfmeister et al. |
| 6,001,065 A | 12/1999 | DeVito |
| 6,021,346 A | 2/2000 | Ryu et al. |
| 6,032,129 A | 2/2000 | Greef et al. |
| 6,052,619 A | 4/2000 | John |
| 6,088,040 A | 7/2000 | Oda et al. |
| 6,099,319 A | 8/2000 | Zaltman et al. |
| 6,120,440 A | 9/2000 | Goknar |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,170,018 B1 | 1/2001 | Voll et al. |
| 6,171,239 B1 | 1/2001 | Humphrey |
| 6,173,260 B1 | 1/2001 | Slaney |
| 6,175,753 B1 | 1/2001 | Menkes et al. |
| 6,212,502 B1 | 4/2001 | Ball et al. |
| 6,228,038 B1 | 5/2001 | Claessens |
| 6,236,885 B1 | 5/2001 | Hunter et al. |
| 6,254,536 B1 | 7/2001 | DeVito |
| 6,280,198 B1 | 8/2001 | Calhoun et al. |
| 6,286,005 B1 | 9/2001 | Cannon |
| 6,289,234 B1 | 9/2001 | Mueller |
| 6,292,688 B1 | 9/2001 | Patton |
| 6,299,308 B1 | 10/2001 | Voronka et al. |
| 6,301,493 B1 | 10/2001 | Marro et al. |
| 6,315,569 B1 | 11/2001 | Zaltman |
| 6,330,470 B1 | 12/2001 | Tucker et al. |
| 6,334,778 B1 | 1/2002 | Brown |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill |
| 6,434,419 B1 | 8/2002 | Gevins et al. |
| 6,435,878 B1 | 8/2002 | Reynolds et al. |
| 6,453,194 B1 | 9/2002 | Hill |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,545,685 B1 | 4/2003 | Dorbie |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,609,024 B1 | 8/2003 | Ryu et al. |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,688,890 B2 | 2/2004 | von Buegner |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopenathan et al. |
| 6,788,882 B1 | 9/2004 | Geer et al. |
| 6,792,304 B1 | 9/2004 | Silberstein |
| 6,842,877 B2 | 1/2005 | Robarts et al. |
| 6,904,408 B1 | 6/2005 | McCarthy et al. |
| 6,950,698 B2 | 9/2005 | Sarkela et al. |
| 6,958,710 B2 | 10/2005 | Zhang et al. |
| 6,973,342 B1 | 12/2005 | Swanson |
| 6,993,380 B1 | 1/2006 | Modarres |
| 7,043,056 B2 | 5/2006 | Edwards et al. |

(56) References Cited

U.S. PATENT DOCUMENTS

| | | |
|---|---|---|
| 7,113,916 B1 | 9/2006 | Hill |
| 7,120,880 B1 | 10/2006 | Dryer et al. |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,177,675 B2 | 2/2007 | Suffin et al. |
| 7,222,071 B2 | 5/2007 | Neuhauser et al. |
| 7,246,081 B2 | 7/2007 | Hill |
| 7,272,982 B2 | 9/2007 | Neuhauser et al. |
| 7,286,871 B2 | 10/2007 | Cohen |
| 7,340,060 B2 | 3/2008 | Tomkins et al. |
| 7,391,835 B1 | 6/2008 | Gross et al. |
| 7,408,460 B2 | 8/2008 | Crystal et al. |
| 7,420,464 B2 | 9/2008 | Fitzgerald et al. |
| 7,443,292 B2 | 10/2008 | Jensen et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,987 B2 | 12/2008 | Crystal et al. |
| 7,483,835 B2 | 1/2009 | Neuhauser et al. |
| 7,483,844 B2 | 1/2009 | Takakura et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,630,757 B2 | 12/2009 | Dorfmeister et al. |
| 7,636,456 B2 | 12/2009 | Collins et al. |
| 7,650,793 B2 | 1/2010 | Jensen et al. |
| 7,658,327 B2 | 2/2010 | Tuchman et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,720,351 B2 | 5/2010 | Levitan |
| 7,729,755 B2 | 6/2010 | Laken |
| 7,809,420 B2 | 10/2010 | Hannula et al. |
| 7,840,248 B2 | 11/2010 | Fuchs et al. |
| 7,840,250 B2 | 11/2010 | Tucker |
| 7,865,394 B1 | 1/2011 | Calloway |
| 7,892,764 B2 | 2/2011 | Xiong et al. |
| 7,908,133 B2 | 3/2011 | Neuhauser |
| 7,917,366 B1 | 3/2011 | Levanon et al. |
| 7,930,199 B1 | 4/2011 | Hill |
| 7,946,974 B2 | 5/2011 | Lordereau |
| 7,962,315 B2 | 6/2011 | Jensen et al. |
| 7,988,557 B2 | 8/2011 | Soderland |
| 8,014,847 B2 | 9/2011 | Shastri et al. |
| 8,027,518 B2 | 9/2011 | Baker et al. |
| 8,055,722 B2 | 11/2011 | Hille |
| 8,060,795 B2 | 11/2011 | Bakekolo et al. |
| 8,069,125 B2 | 11/2011 | Jung et al. |
| 8,079,054 B1 | 12/2011 | Dhawan et al. |
| 8,082,215 B2 | 12/2011 | Jung et al. |
| 8,086,563 B2 | 12/2011 | Jung et al. |
| 8,098,152 B2 | 1/2012 | Zhang et al. |
| 8,103,328 B2 | 1/2012 | Turner et al. |
| 8,135,606 B2 | 3/2012 | Dupree |
| 8,151,298 B2 | 4/2012 | Begeja et al. |
| 8,165,916 B2 | 4/2012 | Hoffberg et al. |
| 8,179,604 B1 | 5/2012 | Prada Gomez et al. |
| 8,209,224 B2 | 6/2012 | Pradeep et al. |
| 8,229,469 B2 | 7/2012 | Zhang et al. |
| 8,235,725 B1 | 8/2012 | Hill |
| 8,239,030 B1 | 8/2012 | Hagedorn et al. |
| 8,255,267 B2 | 8/2012 | Breiter |
| 8,270,814 B2 | 9/2012 | Pradeep et al. |
| 8,300,526 B2 | 10/2012 | Saito et al. |
| 8,326,002 B2 | 12/2012 | Hill |
| 8,327,395 B2 | 12/2012 | Lee |
| 8,332,883 B2 | 12/2012 | Lee |
| 8,335,715 B2 | 12/2012 | Pradeep et al. |
| 8,381,244 B2 | 2/2013 | King |
| 8,386,312 B2 | 2/2013 | Pradeep et al. |
| 8,386,313 B2 | 2/2013 | Pradeep et al. |
| 8,388,165 B2 | 3/2013 | Zhang |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 8,442,429 B2 | 5/2013 | Hawit |
| 8,467,133 B2 | 6/2013 | Miller |
| 8,473,345 B2 | 6/2013 | Pradeep et al. |
| 8,477,425 B2 | 7/2013 | Border et al. |
| 8,484,081 B2 | 7/2013 | Pradeep et al. |
| 8,494,610 B2 | 7/2013 | Pradeep et al. |
| 8,494,905 B2 | 7/2013 | Pradeep et al. |
| 8,548,852 B2 | 10/2013 | Pradeep et al. |
| 8,600,100 B2 | 12/2013 | Hill |
| 8,635,105 B2 | 1/2014 | Pradeep et al. |
| 8,655,428 B2 | 2/2014 | Pradeep et al. |
| 8,655,437 B2 | 2/2014 | Pradeep et al. |
| 8,788,372 B2 | 7/2014 | Kettner et al. |
| 8,793,715 B1 | 7/2014 | Weitzenfeld et al. |
| 2001/0020236 A1 | 9/2001 | Cannon |
| 2001/0029468 A1 | 10/2001 | Yamaguchi et al. |
| 2001/0032140 A1 | 10/2001 | Hoffman |
| 2001/0056225 A1 | 12/2001 | DeVito |
| 2002/0056087 A1 | 5/2002 | Berezowski |
| 2002/0056124 A1 | 5/2002 | Hay |
| 2002/0065826 A1 | 5/2002 | Bell et al. |
| 2002/0072952 A1 | 6/2002 | Hamzey et al. |
| 2002/0077534 A1 | 6/2002 | DuRousseau |
| 2002/0103429 A1 | 8/2002 | deCharms |
| 2002/0143627 A1 | 10/2002 | Barsade et al. |
| 2002/0155878 A1 | 10/2002 | Lert, Jr. et al. |
| 2002/0156842 A1 | 10/2002 | Signes et al. |
| 2002/0188216 A1* | 12/2002 | Kayyali et al. ............... 600/544 |
| 2002/0188217 A1 | 12/2002 | Farwell |
| 2002/0193670 A1 | 12/2002 | Garfield et al. |
| 2003/0013981 A1 | 1/2003 | Gevins et al. |
| 2003/0036955 A1 | 2/2003 | Tanaka |
| 2003/0037333 A1 | 2/2003 | Ghashghai et al. |
| 2003/0059750 A1 | 3/2003 | Bindler et al. |
| 2003/0065524 A1 | 4/2003 | Giacchetti et al. |
| 2003/0073921 A1 | 4/2003 | Sohmer et al. |
| 2003/0081834 A1 | 5/2003 | Philomin et al. |
| 2003/0100998 A2 | 5/2003 | Brunner et al. |
| 2003/0104865 A1 | 6/2003 | Itkis et al. |
| 2003/0165270 A1 | 9/2003 | Endrikhovski et al. |
| 2003/0177488 A1 | 9/2003 | Smith et al. |
| 2003/0208754 A1 | 11/2003 | Sridhar et al. |
| 2003/0233278 A1 | 12/2003 | Marshall |
| 2004/0001616 A1 | 1/2004 | Gutta et al. |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0073129 A1 | 4/2004 | Caldwell et al. |
| 2004/0092809 A1 | 5/2004 | DeCharms |
| 2004/0098298 A1 | 5/2004 | Yin |
| 2004/0101212 A1 | 5/2004 | Fedorovskaya et al. |
| 2004/0187167 A1 | 9/2004 | Maguire et al. |
| 2004/0193068 A1* | 9/2004 | Burton et al. ............... 600/544 |
| 2004/0210159 A1 | 10/2004 | Kibar et al. |
| 2004/0220483 A1 | 11/2004 | Yeo et al. |
| 2004/0236623 A1 | 11/2004 | Gopalakrishnan |
| 2005/0010475 A1 | 1/2005 | Perkowski et al. |
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0143629 A1 | 6/2005 | Farwell |
| 2005/0149964 A1 | 7/2005 | Thomas et al. |
| 2005/0154290 A1 | 7/2005 | Langleben |
| 2005/0177058 A1 | 8/2005 | Sobell |
| 2005/0197590 A1 | 9/2005 | Osorio et al. |
| 2005/0203798 A1 | 9/2005 | Jensen et al. |
| 2005/0216243 A1 | 9/2005 | Graham et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0261980 A1 | 11/2005 | Hadi |

(56) References Cited

U.S. PATENT DOCUMENTS

| | | |
|---|---|---|
| 2005/0267798 A1 | 12/2005 | Panara |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0010470 A1 | 1/2006 | Kurosaki |
| 2006/0035707 A1 | 2/2006 | Nguyen et al. |
| 2006/0053110 A1 | 3/2006 | McDonald et al. |
| 2006/0093998 A1 | 5/2006 | Vertegaal |
| 2006/0111044 A1 | 5/2006 | Keller |
| 2006/0111644 A1 | 5/2006 | Guttag et al. |
| 2006/0129458 A1 | 6/2006 | Maggio |
| 2006/0149337 A1 | 7/2006 | John |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0176289 A1 | 8/2006 | Horn |
| 2006/0190822 A1 | 8/2006 | Basson et al. |
| 2006/0218046 A1 | 9/2006 | Carfi et al. |
| 2006/0256133 A1 | 11/2006 | Rosenberg |
| 2006/0257834 A1 | 11/2006 | Lee et al. |
| 2006/0259360 A1 | 11/2006 | Flinn et al. |
| 2006/0259371 A1 | 11/2006 | Perrier et al. |
| 2006/0293921 A1 | 12/2006 | McCarthy et al. |
| 2007/0016096 A1 | 1/2007 | McNabb |
| 2007/0048707 A1 | 3/2007 | Caamano et al. |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066874 A1 | 3/2007 | Cook |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078706 A1 | 4/2007 | Datta et al. |
| 2007/0079331 A1 | 4/2007 | Datta et al. |
| 2007/0101360 A1 | 5/2007 | Gutta et al. |
| 2007/0106170 A1 | 5/2007 | Dunseath, Jr. et al. |
| 2007/0112460 A1 | 5/2007 | Kiselik |
| 2007/0135727 A1 | 6/2007 | Virtanen et al. |
| 2007/0135728 A1 | 6/2007 | Snyder et al. |
| 2007/0136753 A1 | 6/2007 | Bovenschulte et al. |
| 2007/0150916 A1 | 6/2007 | Begole et al. |
| 2007/0214471 A1 | 9/2007 | Rosenberg |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0250846 A1 | 10/2007 | Swix et al. |
| 2007/0265507 A1 | 11/2007 | de Lemos |
| 2007/0282566 A1 | 12/2007 | Whitlow et al. |
| 2007/0294132 A1 | 12/2007 | Zhang et al. |
| 2007/0294705 A1 | 12/2007 | Gopalakrishnan |
| 2007/0294706 A1 | 12/2007 | Neuhauser et al. |
| 2008/0001600 A1 | 1/2008 | deCharms |
| 2008/0010110 A1 | 1/2008 | Neuhauser et al. |
| 2008/0027345 A1 | 1/2008 | Kumada et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0086356 A1 | 4/2008 | Glassman et al. |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0147488 A1 | 6/2008 | Tunick et al. |
| 2008/0152300 A1 | 6/2008 | Knee et al. |
| 2008/0162182 A1 | 7/2008 | Cazares et al. |
| 2008/0195471 A1 | 8/2008 | Dube |
| 2008/0204273 A1 | 8/2008 | Crystal et al. |
| 2008/0208072 A1 | 8/2008 | Fadem et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2008/0306398 A1 | 12/2008 | Uchiyama et al. |
| 2009/0024049 A1 | 1/2009 | Pradeep et al. |
| 2009/0024447 A1 * | 1/2009 | Pradeep et al. ............. 705/10 |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0060240 A1 | 3/2009 | Coughlan et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0069652 A1 | 3/2009 | Lee et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0082692 A1 | 3/2009 | Hale et al. |
| 2009/0083129 A1 | 3/2009 | Pradeep et al. |
| 2009/0088610 A1 | 4/2009 | Lee et al. |
| 2009/0089830 A1 | 4/2009 | Chandratillake et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0112077 A1 | 4/2009 | Nguyen et al. |
| 2009/0112117 A1 * | 4/2009 | Rewari ............. 600/544 |
| 2009/0119154 A1 | 5/2009 | Jung et al. |
| 2009/0131764 A1 | 5/2009 | Lee et al. |
| 2009/0132441 A1 | 5/2009 | Muller et al. |
| 2009/0133047 A1 | 5/2009 | Lee et al. |
| 2009/0144780 A1 | 6/2009 | Toebes et al. |
| 2009/0150919 A1 | 6/2009 | Lee et al. |
| 2009/0150920 A1 | 6/2009 | Jones |
| 2009/0153328 A1 | 6/2009 | Otani et al. |
| 2009/0156907 A1 | 6/2009 | Jung et al. |
| 2009/0156955 A1 | 6/2009 | Jung et al. |
| 2009/0158308 A1 | 6/2009 | Weitzenfeld et al. |
| 2009/0163777 A1 | 6/2009 | Jung et al. |
| 2009/0164132 A1 | 6/2009 | Jung et al. |
| 2009/0171164 A1 | 7/2009 | Jung et al. |
| 2009/0187467 A1 | 7/2009 | Fang et al. |
| 2009/0195392 A1 | 8/2009 | Zalewski |
| 2009/0214060 A1 | 8/2009 | Chuang et al. |
| 2009/0221928 A1 | 9/2009 | Einav et al. |
| 2009/0248484 A1 | 10/2009 | Surendran et al. |
| 2009/0248496 A1 | 10/2009 | Hueter et al. |
| 2009/0248594 A1 | 10/2009 | Castleman et al. |
| 2009/0249223 A1 | 10/2009 | Barsook et al. |
| 2009/0253996 A1 | 10/2009 | Lee et al. |
| 2009/0259137 A1 | 10/2009 | Delic et al. |
| 2009/0271294 A1 | 10/2009 | Hadi |
| 2009/0287108 A1 | 11/2009 | Levy |
| 2009/0292587 A1 | 11/2009 | Fitzgerald |
| 2009/0300672 A1 | 12/2009 | Van Gulik |
| 2009/0318773 A1 | 12/2009 | Jung et al. |

(56) References Cited

U.S. PATENT DOCUMENTS

| | | |
|---|---|---|
| 2009/0318826 A1 | 12/2009 | Green et al. |
| 2009/0327068 A1 | 12/2009 | Pradeep et al. |
| 2009/0328089 A1 | 12/2009 | Pradeep et al. |
| 2010/0004977 A1 | 1/2010 | Marci et al. |
| 2010/0022821 A1 | 1/2010 | Dubi et al. |
| 2010/0041962 A1 | 2/2010 | Causevic et al. |
| 2010/0042012 A1 | 2/2010 | Alhussiny |
| 2010/0060300 A1 | 3/2010 | Muller et al. |
| 2010/0094702 A1 | 4/2010 | Silberstein |
| 2010/0121716 A1 | 5/2010 | Golan |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0153175 A1 | 6/2010 | Pearson et al. |
| 2010/0169153 A1 | 7/2010 | Hwacinski et al. |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0223094 A1 | 9/2010 | Cumming et al. |
| 2010/0234752 A1* | 9/2010 | Sullivan et al. ............... 600/544 |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0250347 A1 | 9/2010 | Rainier et al. |
| 2010/0250458 A1 | 9/2010 | Ho |
| 2010/0257052 A1 | 10/2010 | Zito et al. |
| 2010/0263005 A1 | 10/2010 | White |
| 2010/0268540 A1 | 10/2010 | Arshi et al. |
| 2010/0268573 A1 | 10/2010 | Jain et al. |
| 2010/0269127 A1 | 10/2010 | Krug |
| 2010/0274152 A1 | 10/2010 | McPeck et al. |
| 2010/0274153 A1 | 10/2010 | Tucker et al. |
| 2010/0306030 A1 | 12/2010 | Mawani |
| 2010/0306120 A1 | 12/2010 | Ciptawilangga |
| 2010/0317988 A1 | 12/2010 | Terada et al. |
| 2010/0318507 A1 | 12/2010 | Grant et al. |
| 2010/0325660 A1 | 12/2010 | Holden |
| 2010/0331661 A1 | 12/2010 | Nakagawa |
| 2011/0004089 A1 | 1/2011 | Chou |
| 2011/0015503 A1 | 1/2011 | Joffe et al. |
| 2011/0022965 A1 | 1/2011 | Lawerence et al. |
| 2011/0040202 A1 | 2/2011 | Luo et al. |
| 2011/0043759 A1 | 2/2011 | Bushinsky |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047035 A1 | 2/2011 | Gidwani et al. |
| 2011/0047121 A1 | 2/2011 | Pradeep et al. |
| 2011/0059422 A1 | 3/2011 | Masaoka |
| 2011/0084795 A1 | 4/2011 | Fukuyori |
| 2011/0085700 A1 | 4/2011 | Lee |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0131274 A1 | 6/2011 | Hille |
| 2011/0144519 A1 | 6/2011 | Causevic |
| 2011/0153391 A1 | 6/2011 | Tenbrock |
| 2011/0153423 A1 | 6/2011 | Elvekrog et al. |
| 2011/0161163 A1 | 6/2011 | Carlson et al. |
| 2011/0161790 A1 | 6/2011 | Junior et al. |
| 2011/0191142 A1 | 8/2011 | Huang |
| 2011/0208515 A1 | 8/2011 | Neuhauser |
| 2011/0224569 A1 | 9/2011 | Isenhart et al. |
| 2011/0237923 A1 | 9/2011 | Picht et al. |
| 2011/0237971 A1 | 9/2011 | Pradeep et al. |
| 2011/0248729 A2 | 10/2011 | Mueller et al. |
| 2011/0256520 A1 | 10/2011 | Siefert |
| 2011/0257502 A1 | 10/2011 | Lee |
| 2011/0257937 A1 | 10/2011 | Lee |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2011/0298706 A1 | 12/2011 | Mann |
| 2011/0301431 A1 | 12/2011 | Greicius |
| 2011/0319975 A1 | 12/2011 | Ho et al. |
| 2012/0002848 A1 | 1/2012 | Hill |
| 2012/0004899 A1 | 1/2012 | Arshi |
| 2012/0022391 A1 | 1/2012 | Leuthardt |
| 2012/0036004 A1 | 2/2012 | Pradeep et al. |
| 2012/0036005 A1 | 2/2012 | Pradeep et al. |
| 2012/0046993 A1 | 2/2012 | Hill |
| 2012/0054018 A1 | 3/2012 | Pradeep et al. |
| 2012/0072289 A1 | 3/2012 | Pradeep et al. |
| 2012/0089552 A1 | 4/2012 | Chang et al. |
| 2012/0096363 A1 | 4/2012 | Barnes et al. |
| 2012/0108995 A1 | 5/2012 | Pradeep et al. |
| 2012/0114305 A1 | 5/2012 | Holden |
| 2012/0130800 A1 | 5/2012 | Pradeep et al. |
| 2012/0173701 A1 | 7/2012 | Tenbrock |
| 2012/0203363 A1 | 8/2012 | McKenna et al. |
| 2012/0203559 A1 | 8/2012 | McKenna et al. |
| 2012/0239407 A1 | 9/2012 | Jain et al. |
| 2012/0245978 A1 | 9/2012 | Crystal et al. |
| 2012/0249797 A1 | 10/2012 | Haddick et al. |
| 2012/0254909 A1 | 10/2012 | Serdiuk |
| 2013/0024272 A1 | 1/2013 | Pradeep et al. |
| 2013/0060125 A1 | 3/2013 | Zeman |
| 2013/0094722 A1 | 4/2013 | Hill |
| 2013/0124365 A1 | 5/2013 | Pradeep |
| 2013/0152506 A1 | 6/2013 | Pradeep |
| 2013/0166373 A1 | 6/2013 | Pradeep et al. |
| 2013/0185140 A1 | 7/2013 | Pradeep et al. |
| 2013/0185141 A1 | 7/2013 | Pradeep et al. |
| 2013/0185142 A1 | 7/2013 | Pradeep et al. |
| 2013/0185144 A1 | 7/2013 | Pradeep et al. |
| 2013/0185145 A1 | 7/2013 | Pradeep et al. |
| 2013/0304540 A1 | 11/2013 | Pradeep et al. |
| 2013/0332259 A1 | 12/2013 | Pradeep et al. |
| 2014/0162225 A1 | 6/2014 | Hill |
| 2014/0350431 A1 | 11/2014 | Hagedorn |

FOREIGN PATENT DOCUMENTS

| | | |
|---|---|---|
| JP | 2005-160805 | 12/2003 |
| JP | 2006-305334 | 3/2006 |
| KR | 200422399 | 7/2006 |
| WO | 95-18565 | 7/1995 |
| WO | 97-17774 | 5/1997 |
| WO | 97-40745 | 11/1997 |
| WO | 97-41673 | 11/1997 |
| WO | 02-100241 | 12/2002 |
| WO | 02-102238 | 12/2002 |
| WO | 2004-049225 | 6/2004 |
| WO | 2008-064431 | 6/2008 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-141340 | 10/2008 |
| WO | 2008-137579 | 11/2008 |
| WO | 2008-137581 | 11/2008 |
| WO | 2008-154410 | 12/2008 |
| WO | 2009-018374 | 2/2009 |
| WO | 2009-052833 | 4/2009 |
| WO | 2011-055291 | 5/2011 |
| WO | 2011-056679 | 5/2011 |

OTHER PUBLICATIONS

Office Action, issued by the United States Patent and Trademark Office in connection with U.S. Appl. No. 13/730,541, on Jan. 30, 2014, 12 pages.

(56) References Cited

OTHER PUBLICATIONS

Office Action, issued by the United States Patent and Trademark Office in connection with U.S. Appl. No. 13/730,550, on Jan. 31, 2014, 5 pages.
Office Action, issued by the United States Patent and Trademark Office in connection with U.S. Appl. No. 13/965,805, on Feb. 3, 2014, 15 pages.
Notice of Allowance, issued by the United States Patent and Trademark Office in connection with U.S. Appl. No. 13/444,149, on Feb. 3, 2014, 5 pages.
Office Action, issued by the United States Patent and Trademark Office in connection with U.S. Appl. No. 12/113,870, on Feb. 4, 2014, 12 pages.
Office Action, issued by the United States Patent and Trademark Office in connection with U.S. Appl. No. 12/546,586, on Feb. 6, 2014, 17 pages.
Office Action, issued by the United States Patent and Trademark Office in connection with U.S. Appl. No. 13/730,564, on Feb. 10, 2014, 14 pages.
Office Action, issued by the United States Patent and Trademark Office in connection with U.S. Appl. No. 112/884,034, on Feb. 10, 2014, 18 pages.
Axis Communications, "Improve your merchandising effectiveness. Get the full picture with network video" (2008), available at :http://www.axis.com/files/user_scenarios/ap_ret_merchandising_31107_en_0803_1o.pdf, 2 pages.
Brown, M. "Should My Advertising Stimulate an Emotional Response?" (2009) available at http://www.wpp.com/~/media/sharedwpp/readingroom/marketing/millward_brown_emotional_response.pdf, 6 pages.
Mehta, A. et al., "Reconsidering Recall and Emotion in Advertising", Journal of Advertising Research, (Mar. 2006), 49-56, 8 pages.
Cheung, Kwok-Wai, et al., "Mining Customer Product Ratings for Personalized Marketing," Decision Support Systems 35 (2003) 231-243, 13 pages.
Notice of Allowance, issued by the United States Patent and Trademark Office in connection with U.S. Appl. No. 13/730,550, on May 27, 2014, 8 pages.
Notice of Allowance, issued by the United States Patent and Trademark Office in connection with U.S. Appl. No. 13/730,511, on May 29, 2014, 8 pages.
Office Action, issued by the United States Patent and Trademark Office in connection with U.S. Appl. No. 12/608,660, on Jun. 2, 2014, 13 pages.
Office Action, issued by the United States Patent and Trademark Office in connection with U.S. Appl. No. 12/122,253, on Jun. 5, 2014, 25 pages.
Final Office Action, issued by the United States Patent and Trademark Office in connection with U.S. Appl. No. 12/113,870, on Jul. 1, 2014, 16 pages.
Decision to Grant Patent, issued by the Japanese Patent Office in connection with Patent Application No. 2010-523112, on Apr. 8, 2014, 4 pages.
English Translation of Office Action, issued by the Israel Patent Office in connection with Patent Application No. 201187, on Apr. 23, 2014, 2 pages.
Darrow, Chester, "Psychological and psychophysiological significance of the electroencephalogram," Psychological Review (May 1947) 157-168, 12 pages.
Stamm, John, "On the Relationship between Reaction Time to Light and Latency of Blocking the Alpha Rhythm," Electroencephalography and Clinical Neurophysiology (Feb. 1952), 61-68, 8 pages.
Mizuki, Yashushi, et al., "Periodic Appearance of the Theta Rhythm in the Frontal Midline Area During Performance of a Mental Task,:" Electroencephalography and Clinical Neurophysiology (Aug. 1980), 345-351, 7 pages.
Extended European Search Report, issued by the European Patent Office in connection with European Application No. 08744383.4-2221/2130146, on Jul. 27, 2011, 6 pages.
Extended European Search Report, issued by the European Patent Office in connection with European Application No. 10173095.0-2221, on Dec. 17, 2010, 3 pages.
Extended European Search Report, issued by the European Patent Office in connection with European Application No. 10189294.1-2221, on Mar. 21, 2011, 7 pages.
First Office Action, issued by the State Intellectual Property Office of P.R. China in connection with Patent Application No. 200880104982.1, on Jan. 25, 2011, 15 pages.
First Office Action, issued by the State Intellectual Property Office of P.R. China in connection with Patent Application No. 2008801015007, on May 25, 2011, 8 pages.
First Office Action, issued by the State Intellectual Property Office of P.R. China in connection with Patent Application No. 200880019166.0, on Jul. 22, 2011, 16 pages.
Decision of Rejection, issued by the State Intellectual Property Office of P.R. China in connection with Patent Application No. 200880104982.1, on Sep. 23, 2011, 10 pages.
Extended European Search Report, issued by the European Patent Office in connection with European Application No. 11006934.1-2221, on Oct. 25, 2011, 5 pages.
First Office Action, issued by the State Intellectual Property Office of P.R. China in connection with Patent Application No. 20080017883.X, on Nov. 30, 2011, 16 pages.
English Translation of Office Action, issued by the Israel Patent Office in connection with Patent Application No. 203176, on Feb. 21, 2012, 2 pages.
English Translation of Office Action, issued by the Israel Patent Office in connection with Patent Application No. 203177, on Mar. 1, 2012, 2 pages.
Second Office Action, issued by the State Intellectual Property Office of P.R. China in connection with Patent Application No. 200880101500.7, on Apr. 5, 2012, 5 pages.
Second Office Action, issued by the State Intellectual Property Office of P.R. China in connection with Patent Application No. 200880019166.0, on Jun. 5, 2012, 8 pages.
Second Office Action, issued by the State Intellectual Property Office of P.R. China in connection with Patent Application No. 200880104982.1, on Jun. 29, 2012, 5 pages.
Second Office Action, issued by the State Intellectual Property Office of P.R. China in connection with Patent Application No. 200880017883.X, on Aug. 10, 2012, 9 pages.
English Translation of Office Action, issued by the Israel Patent Office in connection with Patent Application No. 203176, on Sep. 27, 2012, 1 pages.
English Translation of Office Action, issued by the Israel Patent Office in connection with Patent Application No. 203177, on Sep. 27, 2012, 1 pages.
Office Action, issued by the Japanese Patent Office in connection with Patent Application No. 2010-501190, on Oct. 5, 2012, 5 pages.
English Translation of Office Action, issued by the Japanese Patent Office in connection with Patent Application No. 2010-506646, on Oct. 23, 2012, 3 pages.
English Translation of Third Office Action, issued by the State Intellectual Property Office of P.R. China in connection with Patent Application No. 200880101500.7, on Nov. 21, 2012, 5 pages.
English Translation of Office Action, issued by the Israeli Patent Office in connection with Patent Application No. 201187, on Nov. 27, 2012, 2 pages.
Extended European Search Report, issued by the European Patent Office in connection with European Application No. 08796890.5-2319/2170161, on Dec. 7, 2012, 9 pages.
Notification to Grant Patent Right for Invention, issued by the State Intellectual Property Office of P.R. China in connection with Patent Application No. 200880104982.1, on Jan. 14, 2013, 2 pages.
Extended European Search Report, issued by the European Patent Office in connection with European Application No. 08770372.4-1265/2152155, on Feb. 6, 2013, 7 pages.
English Translation of Third Office Action, issued by the State Intellectual Property Office of P.R. China in connection with Patent Application No. 200880017883.X, on Mar. 18, 2013, 8 pages.

(56) References Cited

OTHER PUBLICATIONS

Notification to Grant Patent Right for Invention, issued by the State Intellectual Property Office of P.R. China in connection with Patent Application No. 200880101500.7, on Apr. 3, 2013, 2 pages.
English Translation of Office Action, issued by the Israeli Patent Office in connection with Patent Application No. 203176, on Apr. 23, 2013, 1 page.
English Translation of Notice Prior to Allowance, issued by the Israeli Patent Office in connection with Patent Application No. 203176, on Jun. 30, 2013, 1 page.
English Translation of Office Action, issued by the Japanese Patent Office in connection with Patent Application No. 2010-523112, on Jul. 30, 2013, 2 pages.
Decision to Grant Patent, issued by the Japanese Patent Office in connection with Patent Application No. 2010506645, on Aug. 12, 2013, 3 pages.
English Translation of Decision on Rejection, issued by the Chinese Patent Office in connection with Patent Application No. 200880017883.X, on Aug. 5, 2013, 13 pages.
English Translation of Office Action, issued by the Japanese Patent Office in connection with Patent Application No. 2010-520159, on Oct. 1, 2013, 2 pages.
Extended European Search Report, issued by the European Patent Office in connection with European Application No. 08798799.6-1657/2180825, on Nov. 4, 2013, 9 pages.
Final Rejection, issued by the United States Patent and Trademark Office in connection with U.S. Appl. No. 12/056,211, on Jul. 8, 2011, 16 pages.
Office Action, issued by the United States Patent and Trademark Office in connection with U.S. Appl. No. 12/056,211, on Jan. 7, 2011, 19 pages.
Office Action issued by the United States Patent and Trademark Office in connection with U.S. Appl. No. 12/056,221, on Apr. 15, 2011, 24 pages.
Final Rejection, issued by the United States Patent and Trademark Office in connection with U.S. Appl. No. 12/113,863, on Jun. 9, 2011, 12 pages.
Office Action, issued by the United States Patent and Trademark Office in connection with U.S. Appl. No. 12/113,863, on Dec. 27, 2010, 15 pages.
Final Rejection, issued by the United States Patent and Trademark Office in connection with U.S. Appl. No. 12/113,870, on Apr. 21, 2011, 10 pages.
Office Action, issued by the United States Patent and Trademark Office in connection with U.S. Appl. No. 12/113,870, on Dec. 3, 2010, 12 pages.
Office Action, issued by the United States Patent and Trademark Office in connection with U.S. Appl. No. 12/122,240, on Jun. 10, 2011, 12 pages.
Final Rejection, issued by the United States Patent and Trademark Office in connection with U.S. Appl. No. 12/122,262, on May 26, 2011, 15 pages.
Office Action, issued by the United States Patent and Trademark Office in connection with U.S. Appl. No. 12/122,262, on Dec. 9, 2010, 13 pages.
Final Rejection, issued by the United States Patent and Trademark Office in connection with U.S. Appl. No. 12/135,066, on Jan. 21, 2011, 16 pages.
Office Action, issued by the United States Patent and Trademark Office in connection with U.S. Appl. No. 12/135,066, on Oct. 28, 2010, 14 pages.
Notice of Panel Decision from Pre-Appeal Brief Review, issued by the United States Patent and Trademark Office in connection with U.S. Appl. No. 12/135,066, on May 31, 2011, 2 pages.
Office Action, issued by the United States Patent and Trademark Office in connection with U.S. Appl. No. 12/135,074, on Dec. 23, 2010, 14 pages.
Final Rejection, issued by the United States Patent and Trademark Office in connection with U.S. Appl. No. 12/135,074, on Jun. 9, 2011, 10 pages.
Final Rejection, issued by the United States Patent and Trademark Office in connection with U.S. Appl. No. 12/182,874, on Jul. 7, 2011, 14 pages.
Office Action, issued by the United States Patent and Trademark Office in connection with U.S. Appl. No. 12/182,874, on Dec. 27, 2010, 17 pages.
Office Action, issued by the United States Patent and Trademark Office in connection with U.S. Appl. No. 12/199,557, on Dec. 27, 2010, 14 pages.
Final Rejection, issued by the United States Patent and Trademark Office in connection with U.S. Appl. No. 12/199,557, on Jun. 9, 2011, 12 pages.
Final Rejection, issued by the United States Patent and Trademark Office in connection with U.S. Appl. No. 12/199,583, on Jun. 21, 2011, 14 pages.
Office Action, issued by the United States Patent and Trademark Office in connection with U.S. Appl. No. 12/199,583, on Dec. 27, 2010, 17 pages.
Final Rejection, issued by the United States Patent and Trademark Office in connection with U.S. Appl. No. 12/199,596, on Jun. 14, 2011, 13 pages.
Office Action, issued by the United States Patent and Trademark Office in connection with U.S. Appl. No. 12/199,596, on Dec. 27, 2010, 17 pages.
Final Rejection, issued by the United States Patent and Trademark Office in connection with U.S. Appl. No. 12/200,813, on Jul. 6, 2011, 13 pages.
Office Action, issued by the United States Patent and Trademark Office in connection with U.S. Appl. No. 12/200,813, on Dec. 27, 2010, 14 pages.
Office Action, issued by the United States Patent and Trademark Office in connection with U.S. Appl. No. 12/234,372, on Jun. 7, 2011, 10 pages.
Final Rejection, issued by the United States Patent and Trademark Office in connection with U.S. Appl. No. 12/135,069, on Feb. 17, 2011, 32 pages.
Office Action, issued by the United States Patent and Trademark Office in connection with U.S. Appl. No. 12/135,069, on Oct. 29, 2010, 21 pages.
Office Action, issued by the United States Patent and Trademark Office in connection with U.S. Appl. No. 12/357,315, on May 4, 2011, 9 pages.
Office Action, issued by the United States Patent and Trademark Office in connection with U.S. Appl. No. 12/410,380, on Jun. 7, 2011, 9 pages.
Office Action, issued by the United States Patent and Trademark Office in connection with U.S. Appl. No. 12/413,297, on Jul. 18, 2011, 9 pages.
Office Action, issued by the United States Patent and Trademark Office in connection with U.S. Appl. No. 12/608,685, on Jul. 12, 2011, 15 pages.
Office Action, issued by the United States Patent and Trademark Office in connection with U.S. Appl. No. 12/056,190, on Aug. 10, 2011, 28 pages.
Office Action, issued by the United States Patent and Trademark Office in connection with U.S. Appl. No. 12/357,322, on Aug. 23, 2011, 12 pages.
Office Action, issued by the United States Patent and Trademark Office in connection with U.S. Appl. No. 12/135,069, on Aug. 26, 2011, 33 pages.
Restriction Requirement, issued by the United States Patent and Trademark Office in connection with U.S. Appl. No. 12/122,253, on Sep. 2, 2011, 7 pages.
Office Action, issued by the United States Patent and Trademark Office in connection with U.S. Appl. No. 12/410,372, on Sep. 12, 2011, 12 pages.
Restriction Requirement, issued by the United States Patent and Trademark Office in connection with U.S. Appl. No. 12/182,851, on Sep. 12, 2011, 7 pages.
Office Action, issued by the United States Patent and Trademark Office in connection with U.S. Appl. No. 12/135,066, on Sep. 29, 2011, 37 pages.

(56) References Cited

OTHER PUBLICATIONS

Restriction Requirement, issued by the United States Patent and Trademark Office in connection with U.S. Appl. No. 12/056,225, on Oct. 3, 2011, 6 pages.
Office Action, issued by the United States Patent and Trademark Office in connection with U.S. Appl. No. 12/234,388, on Oct. 12, 2011, 27 pages.
Office Action, issued by the United States Patent and Trademark Office in connection with U.S. Appl. No. 12/234,372, on Oct. 13, 2011, 22 pages.
Office Action, issued by the United States Patent and Trademark Office in connection with U.S. Appl. No. 12/410,380, on Oct. 19, 2011, 21 pages.
Office Action, issued by the United States Patent and Trademark Office in connection with U.S. Appl. No. 12/357,315, on Oct. 26, 2011, 41 pages.
Office Action, issued by the United States Patent and Trademark Office in connection with U.S. Appl. No. 12/122,240, on Oct. 27, 2011, 39 pages.
Final Rejection, issued by the United States Patent and Trademark Office in connection with U.S. Appl. No. 12/056,221, on Nov. 28, 2011, 44 pages.
Office Action, issued by the United States Patent and Trademark Office in connection with U.S. Appl. No. 12/608,660, on Dec. 7, 2011, 8 pages.
Office Action, issued by the United States Patent and Trademark Office in connection with U.S. Appl. No. 12/113,863, on Dec. 22, 2011, 17 pages.
Office Action, issued by the United States Patent and Trademark Office in connection with U.S. Appl. No. 12/122,262, on Dec. 22, 2011, 17 pages.
Office Action, issued by the United States Patent and Trademark Office in connection with U.S. Appl. No. 12/135,074, on Dec. 22, 2011, 16 pages.
Office Action, issued by the United States Patent and Trademark Office in connection with U.S. Appl. No. 12/199,557, on Dec. 22, 2011, 17 pages.
Office Action, issued by the United States Patent and Trademark Office in connection with U.S. Appl. No. 12/199,596, on Dec. 22, 2011, 15 pages.
Office Action, issued by the United States Patent and Trademark Office in connection with U.S. Appl. No. 12/200,813, on Dec. 22, 2011, 18 pages.
Office Action, issued by the United States Patent and Trademark Office in connection with U.S. Appl. No. 12/199,583, on Dec. 29, 2011, 18 pages.
Final Rejection, issued by the United States Patent and Trademark Office in connection with U.S. Appl. No. 12/410,372, on Jan. 3, 2012, 10 pages.
Final Rejection, issued by the United States Patent and Trademark Office in connection with U.S. Appl. No. 12/413,297, on Jan. 4, 2012, 10 pages.
Office Action, issued by the United States Patent and Trademark Office in connection with U.S. Appl. No. 12/544,921, on Jan. 9, 2012, 13 pages.
Office Action, issued by the United States Patent and Trademark Office in connection with U.S. Appl. No. 12/357,302, on Jan. 17, 2012, 11 pages.
Office Action, issued by the United States Patent and Trademark Office in connection with U.S. Appl. No. 12/056,225, on Jan. 20, 2012, 12 pages.
Final Rejection, issued by the United States Patent and Trademark Office in connection with U.S. Appl. No. 12/135,066, on Jan. 24, 2012, 12 pages.
Office Action, issued by the United States Patent and Trademark Office in connection with U.S. Appl. No. 12/546,586, on Feb. 1, 2012, 17 pages.
Restriction Requirement, issued by the United States Patent and Trademark Office in connection with U.S. Appl. No. 12/544,958, on Feb. 10, 2012, 6 pages.
Final Rejection, issued by the United States Patent and Trademark Office in connection with U.S. Appl. No. 12/135,069, on Feb. 14, 2012, 36 pages.
Final Rejection, issued by the United States Patent and Trademark Office in connection with U.S. Appl. No. 12/357,322, on Feb. 14, 2012, 14 pages.
Office Action, issued by the United States Patent and Trademark Office in connection with U.S. Appl. No. 12/056,211, on Feb. 16, 2012, 16 pages.
Final Rejection, issued by the United States Patent and Trademark Office in connection with U.S. Appl. No. 12/056,190, on Feb. 17, 2012, 22 pages.
Office Action, issued by the United States Patent and Trademark Office in connection with U.S. Appl. No. 12/122,253, on Feb. 17, 2012, 20 pages.
Office Action, issued by the United States Patent and Trademark Office in connection with U.S. Appl. No. 12/182,874, on Feb. 17, 2012, 15 pages.
Office Action, issued by the United States Patent and Trademark Office in connection with U.S. Appl. No. 12/868,531, on Mar. 1, 2012, 7 pages.
Office Action, issued by the United States Patent and Trademark Office in connection with U.S. Appl. No. 12/182,851, on Mar. 14, 2012, 17 pages.
Office Action, issued by the United States Patent and Trademark Office in connection with U.S. Appl. No. 12/608,685, on Mar. 29, 2012, 17 pages.
Office Action, issued by the United States Patent and Trademark Office in connection with U.S. Appl. No. 12/846,242, on Mar. 29, 2012, 16 pages.
Office Action, issued by the United States Patent and Trademark Office in connection with U.S. Appl. No. 12/234,388, on Apr. 6, 2012, 6 pages.
Office Action, issued by the United States Patent and Trademark Office in connection with U.S. Appl. No. 12/357,3158, on Apr. 9, 2012, 17 pages.
Office Action, issued by the United States Patent and Trademark Office in connection with U.S. Appl. No. 12/544,958, on May 2, 2012, 15 pages.
Notice of Allowance, issued by the United States Patent and Trademark Office in connection with U.S. Appl. No. 12/357,302, on May 7, 2012, 11 pages.
Notice of Allowance, issued by the United States Patent and Trademark Office in connection with U.S. Appl. No. 12/868,531, on May 8, 2012, 11 pages.
Notice of Allowance, issued by the United States Patent and Trademark Office in connection with U.S. Appl. No. 12/608,696, on May 15, 2012, 6 pages.
Restriction Requirement, issued by the United States Patent and Trademark Office in connection with U.S. Appl. No. 12/545,455, on Jun. 13, 2012, 5 pages.
Office Action, issued by the United States Patent and Trademark Office in connection with U.S. Appl. No. 12/056,225, on Jun. 15, 2012, 9 pages.
Office Action, issued by the United States Patent and Trademark Office in connection with U.S. Appl. No. 12/544,934, on Jun. 18, 2012, 11 pages.
Office Action, issued by the United States Patent and Trademark Office in connection with U.S. Appl. No. 12/135,066, on Jun. 21, 2012, 10 pages.
Final Rejection, issued by the United States Patent and Trademark Office in connection with U.S. Appl. No. 12/608,660, on Jul. 10, 2012, 14 pages.
Final Rejection, issued by the United States Patent and Trademark Office in connection with U.S. Appl. No. 12/608,685, on Jul. 30, 2012, 15 pages.
Examiner's Answer, issued by the United States Patent and Trademark Office in connection with U.S. Appl. No. 12/410,372, on Aug. 3, 2012, 8 pages.
Examiner's Answer, issued by the United States Patent and Trademark Office in connection with U.S. Appl. No. 12/410,380, on Jun. 8, 2012, 12 pages.

(56) References Cited

OTHER PUBLICATIONS

Examiner's Answer, issued by the United States Patent and Trademark Office in connection with U.S. Appl. No. 12/234,372, on May 23, 2012, 11 pages.
Advisory Action, issued by the United States Patent and Trademark Office in connection with U.S. Appl. No. 12/234,388, on Aug. 28, 2012, 3 pages.
Office Action, issued by the United States Patent and Trademark Office in connection with U.S. Appl. No. 12/545,455, on Aug. 29, 2012, 11 pages.
Office Action, issued by the United States Patent and Trademark Office in connection with U.S. Appl. No. 12/778,828, on Aug. 30, 2012, 9 pages.
Office Action, issued by the United States Patent and Trademark Office in connection with U.S. Appl. No. 12/778,810, on Aug. 31, 2012, 12 pages.
Notice of Allowance, issued by the United States Patent and Trademark Office in connection with U.S. Appl. No. 12/056,190, on Sep. 17, 2012, 11 pages.
Notice of Allowance, issued by the United States Patent and Trademark Office in connection with U.S. Appl. No. 12/122,262, on Sep. 17, 2012, 11 pages.
Final Rejection, issued by the United States Patent and Trademark Office in connection with U.S. Appl. No. 12/122,253, on Sep. 17, 2012, 17 pages.
Examiner's Answer, issued by the United States Patent and Trademark Office in connection with U.S. Appl. No. 12/413,297, on Sep. 18, 2012, 18 pages.
Final Rejection, issued by the United States Patent and Trademark Office in connection with U.S. Appl. No. 12/546,586, on Sep. 18, 2012, 17 pages.
Notice of Allowance, issued by the United States Patent and Trademark Office in connection with U.S. Appl. No. 12/056,211, on Sep. 19, 2012, 10 pages.
Notice of Allowance, issued by the United States Patent and Trademark Office in connection with U.S. Appl. No. 12/135,074, on Sep. 19, 2012, 10 pages.
Notice of Allowance, issued by the United States Patent and Trademark Office in connection with U.S. Appl. No. 12/853,213, on Sep. 7, 2012, 9 pages.
Notice of Allowance, issued by the United States Patent and Trademark Office in connection with U.S. Appl. No. 12/199,583, on Sep. 26, 2012, 14 pages.
Notice of Allowance, issued by the United States Patent and Trademark Office in connection with U.S. Appl. No. 12/199,596, on Sep. 27, 2012, 14 pages.
Notice of Allowance, issued by the United States Patent and Trademark Office in connection with U.S. Appl. No. 12/199,557, on Sep. 28, 2012, 12 pages.
Notice of Allowance, issued by the United States Patent and Trademark Office in connection with U.S. Appl. No. 12/113,863, on Oct. 1, 2012, 12 pages.
Office Action, issued by the United States Patent and Trademark Office in connection with U.S. Appl. No. 13/444,149, on Oct. 4, 2012, 9 pages.
Final Office Action, issued by the United States Patent and Trademark Office in connection with U.S. Appl. No. 12/182,851, on Oct. 4, 2012, 14 pages.
Office Action, issued by the United States Patent and Trademark Office in connection with U.S. Appl. No. 12/234,388, on Oct. 5, 2012, 6 pages.
Notice of Allowance, issued by the United States Patent and Trademark Office in connection with U.S. Appl. No. 12/853,197, on Oct. 16, 2012, 5 pages.
Notice of Allowance, issued by the United States Patent and Trademark Office in connection with U.S. Appl. No. 12/868,531, on Oct. 22, 2012, 5 pages.
Final Office Action, issued by the United States Patent and Trademark Office in connection with U.S. Appl. No. 12/846,242, on Nov. 29, 2012, 14 pages.
Notice of Allowance, issued by the United States Patent and Trademark Office in connection with U.S. Appl. No. 12/200,813, on Oct. 30, 2012, 5 pages.
Notice of Allowance, issued by the United States Patent and Trademark Office in connection with U.S. Appl. No. 12/056,190, on Nov. 2, 2012, 5 pages.
Restriction Requirement, issued by the United States Patent and Trademark Office in connection with U.S. Appl. No. 12/056,225, on Nov. 2, 2012, 5 pages.
Final Office Action, issued by the United States Patent and Trademark Office in connection with U.S. Appl. No. 12/135,066, on Nov. 13, 2012, 9 pages.
Notice of Allowance, issued by the United States Patent and Trademark Office in connection with U.S. Appl. No. 12/113,863, on Nov. 16, 2012, 5 pages.
Notice of Allowance, issued by the United States Patent and Trademark Office in connection with U.S. Appl. No. 12/056,211, on Nov. 21, 2012, 5 pages.
Notice of Allowance, issued by the United States Patent and Trademark Office in connection with U.S. Appl. No. 12/868,531, on Nov. 23, 2012, 5 pages.
Office Action, issued by the United States Patent and Trademark Office in connection with U.S. Appl. No. 12/913,102, on Dec. 7, 2012, 7 pages.
Final Office Action, issued by the United States Patent and Trademark Office in connection with U.S. Appl. No. 12/544,958, on Dec. 10, 2012, 16 pages.
Notice of Allowance, issued by the United States Patent and Trademark Office in connection with U.S. Appl. No. 12/853,197, on Dec. 20, 2012, 5 pages.
Notice of Allowance, issued by the United States Patent and Trademark Office in connection with U.S. Appl. No. 12/056,190, on Dec. 21, 2012, 14 pages.
Notice of Allowance, issued by the United States Patent and Trademark Office in connection with U.S. Appl. No. 12/056,211, on Dec. 21, 2012, 10 pages.
Notice of Allowance, issued by the United States Patent and Trademark Office in connection with U.S. Appl. No. 12/122,262, on Dec. 21, 2012, 19 pages.
Notice of Allowance, issued by the United States Patent and Trademark Office in connection with U.S. Appl. No. 12/135,074, on Dec. 21, 2012, 12 pages.
Notice of Allowance, issued by the United States Patent and Trademark Office in connection with U.S. Appl. No. 12/199,557, on Dec. 21, 2012, 14 pages.
Notice of Allowance, issued by the United States Patent and Trademark Office in connection with U.S. Appl. No. 12/199,596, on Dec. 21, 2012, 17 pages.
Notice of Allowance, issued by the United States Patent and Trademark Office in connection with U.S. Appl. No. 12/200,813, on Dec. 21, 2012, 9 pages.
Notice of Allowance, issued by the United States Patent and Trademark Office in connection with U.S. Appl. No. 12/853,213, on Dec. 21, 2012, 10 pages.
Notice of Allowance, issued by the United States Patent and Trademark Office in connection with U.S. Appl. No. 12/868,531, on Dec. 26, 2012, 2 pages.
Notice of Allowance, issued by the United States Patent and Trademark Office in connection with U.S. Appl. No. 12/113,863, on Dec. 31, 2012, 5 pages.
Notice of Allowance, issued by the United States Patent and Trademark Office in connection with U.S. Appl. No. 12/199,583, on Dec. 31, 2012, 10 pages.
Final Office Action, issued by the United States Patent and Trademark Office in connection with U.S. Appl. No. 12/182,874, on Jan. 4, 2013, 17 pages.
Notice of Allowance, issued by the United States Patent and Trademark Office in connection with U.S. Appl. No. 12/199,583, on Jan. 11, 2013, 11 pages.
Final Office Action, issued by the United States Patent and Trademark Office in connection with U.S. Appl. No. 12/056,225, on Jan. 11, 2013, 11 pages.

(56) References Cited

OTHER PUBLICATIONS

Recertified IDS and Interview Summary, issued by the United States Patent and Trademark Office in connection with U.S. Appl. No. 12/853,197, on Jan. 16, 2013, 6 pages.
Notice of Allowance, issued by the United States Patent and Trademark Office in connection with U.S. Appl. No. 12/199,557, on Jan. 29, 2013, 17 pages.
Notice of Allowance, issued by the United States Patent and Trademark Office in connection with U.S. Appl. No. 12/85,3197, on Jan. 29, 2013, 11 pages.
Notice of Allowance, issued by the United States Patent and Trademark Office in connection with U.S. Appl. No. 12/056,190, on Jan. 31, 2013, 5 pages.
Notice of Allowance, issued by the United States Patent and Trademark Office in connection with U.S. Appl. No. 12/113,863, on Jan. 31, 2013, 5 pages.
Notice of Allowance, issued by the United States Patent and Trademark Office in connection with U.S. Appl. No. 12/135,074, on Jan. 31, 2013, 10 pages.
Notice of Allowance, issued by the United States Patent and Trademark Office in connection with U.S. Appl. No. 12/199,583, on Feb. 1, 2013, 11 pages.
Notice of Allowance, issued by the United States Patent and Trademark Office in connection with U.S. Appl. No. 12/200,813, on Feb. 1, 2013, 5pages.
Notice of Allowance, issued by the United States Patent and Trademark Office in connection with U.S. Appl. No. 12/056,211, on Feb. 4, 2013, 5 pages.
Notice of Allowance, issued by the United States Patent and Trademark Office in connection with U.S. Appl. No. 12/122,262, on Feb. 5, 2013, 15 pages.
Notice of Allowance, issued by the United States Patent and Trademark Office in connection with U.S. Appl. No. 12/868,531, on Feb. 5, 2013, 8 pages.
Notice of Allowance, issued by the United States Patent and Trademark Office in connection with U.S. Appl. No. 12/853,213, on Feb. 5, 2013, 10 pages.
Notice of Allowance, issued by the United States Patent and Trademark Office in connection with U.S. Appl. No. 12/234,388, on Feb. 15, 2013, 9 pages.
Notice of Allowance, issued by the United States Patent and Trademark Office in connection with U.S. Appl. No. 12/056,190, on Feb. 14, 2013, 5 pages.
Notice of Allowance, issued by the United States Patent and Trademark Office in connection with U.S. Appl. No. 12/200,813, on Sep. 20, 2012, 11 pages.
Notice of Allowance, issued by the United States Patent and Trademark Office in connection with U.S. Appl. No. 12/182,874, on Apr. 16, 2013, 10 pages.
Notice of Allowance, issued by the United States Patent and Trademark Office in connection with U.S. Appl. No. 12/182,874, on Apr. 22, 2013, 11 pages.
Non-Final Office Action, issued by the United States Patent and Trademark Office in connection with U.S. Appl. No. 12/546,586, on Apr. 25, 2013, 34 pages.
Non-Final Office Action, issued by the United States Patent and Trademark Office in connection with U.S. Appl. No. 13/444,149, on May 2, 2013, 27 pages.
Notice of Allowance, issued by the United States Patent and Trademark Office in connection with U.S. Appl. No. 12/056,190, on May 8, 2013, 4 pages.
Notice of Allowance, issued by the United States Patent and Trademark Office in connection with U.S. Appl. No. 12/056,211, on May 8, 2013, 5 pages.
Notice of Allowance, issued by the United States Patent and Trademark Office in connection with U.S. Appl. No. 12/135,074, on May 8, 2013, 5 pages.
Notice of Allowance, issued by the United States Patent and Trademark Office in connection with U.S. Appl. No. 12/199,596, on May 8, 2013, 7 pages.
Notice of Allowance, issued by the United States Patent and Trademark Office in connection with U.S. Appl. No. 13/569,711, on May 14, 2013, 6 pages.
Notice of Allowance, issued by the United States Patent and Trademark Office in connection with U.S. Appl. No. 12/182,874, on May 17, 2013, 6 pages.
Notice of Allowance, issued by the United States Patent and Trademark Office in connection with U.S. Appl. No. 12/135,074, on May 31, 2013, 5 pages.
Notice of Allowance, issued by the United States Patent and Trademark Office in connection with U.S. Appl. No. 12/056,211, on Jun. 3, 2013, 5 pages.
Notice of Allowance, issued by the United States Patent and Trademark Office in connection with U.S. Appl. No. 12/199,596, on Jun. 3, 2013, 5 pages.
Notice of Allowance, issued by the United States Patent and Trademark Office in connection with U.S. Appl. No. 12/199,596, on Jun. 11, 2013, 7 pages.
Notice of Allowance, issued by the United States Patent and Trademark Office in connection with U.S. Appl. No. 12/545,455, on Jun. 11, 2013, 9 pages.
Notice of Allowance, issued by the United States Patent and Trademark Office in connection with U.S. Appl. No. 12/056,190, on Jun. 13, 2013, 5 pages.
Office Communication to Applicant, issued by the United States Patent and Trademark Office in connection with U.S. Appl. No. 12/234,388, on Jun. 13, 2013, 2 pages.
Notice of Allowance, issued by the United States Patent and Trademark Office in connection with U.S. Appl. No. 12/135,074, on Jun. 21, 2013, 5 pages.
Non-Final Office Action, issued by the United States Patent and Trademark Office in connection with U.S. Appl. No. 13/105,774, on Jun. 26, 2013, 10 pages.
Notice of Allowance, issued by the United States Patent and Trademark Office in connection with U.S. Appl. No. 12/182,874, on Jul. 29, 2013, 6 pages.
Notice of Allowance, issued by the United States Patent and Trademark Office in connection with U.S. Appl. No. 12/199,596, on Sep. 13, 2013, 7 pages.
Office Action, issued by the United States Patent and Trademark Office in connection with U.S. Appl. No. 12/546,586, on Sep. 12, 2013, 13 pages.
Office Action, issued by the United States Patent and Trademark Office in connection with U.S. Appl. No. 12/113,870, on Sep. 17, 2013, 11 pages.
Notice of Allowance, issued by the United States Patent and Trademark Office in connection with U.S. Appl. No. 12/778,828, on Oct. 8, 2013, 11 pages.
Final Office Action, issued by the United States Patent and Trademark Office in connection with U.S. Appl. No. 12/884,034, on Oct. 23, 2013, 17 pages.
Notice of Allowance, issued by the United States Patent and Trademark Office in connection with U.S. Appl. No. 12/199,596, on Nov. 6, 2013, 7 pages.
Final Office Action, issued by the United States Patent and Trademark Office in connection with U.S. Appl. No. 13/444,149, on Nov. 19, 2013, 11 pages.
Non-Final Office Action, issued by the United States Patent and Trademark Office in connection with U.S. Appl. No. 12/122,253, on Dec. 3, 2013, 16 pages.
Notice of Allowance, issued by the United States Patent and Trademark Office in connection with U.S. Appl. No. 12/199,596, on Dec. 23, 2013, 7 pages.
Final Office Action, issued by the United States Patent and Trademark Office in connection with U.S. Appl. No. 13/105,774, on Jan. 16, 2014, 11 pages.
International Preliminary Report on Patentability, issued by the International Bureau of WIPO in connection with International Application No. PCT/US08/058264, on Sep. 29, 2009, 1 page.
International Search Report, issued by the International Searching Authority in connection with International Application No. PCT/US08/058264, on Aug. 1, 2008, 2 pages.

(56) References Cited

OTHER PUBLICATIONS

Written Opinion, issued by the International Searching Authority in connection with International Application No. PCT/US08/058264, on Aug. 1, 2008, 5 pages.
International Preliminary Report on Patentability, issued by the International Bureau of WIPO in connection with International Application No. PCT/US08/062273, on Nov. 3, 2009, 1 page.
International Search Report, issued by the International Searching Authority in connection with International Application No. PCT/US08/062273, on Sep. 5, 2008, 2 pages.
Written Opinion, issued by the International Searching Authority in connection with International Application No. PCT/US08/062273, on Sep. 5, 2008, 4 pages.
International Search Report, issued by the International Bureau in connection with International Application No. PCT/US08/062275, on Sep. 22, 2008, 2 pages.
Written Opinion, issued by the International Bureau in connection with International Application No. PCT/US08/062275, on Sep. 22, 2008, 6 pages.
International Preliminary Report on Patentability, issued by the International Bureau of WIPO in connection with International Application No. PCT/US08/063984, on Nov. 17, 2009, 1 page.
International Search Report, issued by the International Bureau in connection with International Application No. PCT/US08/063984, on Sep. 29, 2008, 3 pages.
Written Opinion, issued by the International Bureau in connection with International Application No. PCT/US08/063984, on Sep. 29, 2008, 4 pages.
International Preliminary Report on Patentability, issued by the International Bureau of WIPO in connection with International Application No. PCT/US08/063989, on Nov. 17, 2009, 1 page.
International Search Report, issued by the International Bureau in connection with International Application No. PCT/US08/063989, on Jul. 17, 2008, 2 pages.
Written Opinion, issued by the International Bureau in connection with International Application No. PCT/US08/063989, on Jul. 17, 2008, 4 pages.
International Preliminary Report on Patentability, issued by the International Bureau of WIPO in connection with International Application No. PCT/US08/066166, on Dec. 7, 2009, 1 page.
International Search Report, issued by the International Bureau in connection with International Application No. PCT/US08/066166, on Aug. 25, 2008, 2 pages.
Written Opinion, issued by the International Bureau in connection with International Application No. PCT/US08/066166, on Aug. 25, 2008, 6 pages.
International Preliminary Report on Patentability, issued by the International Bureau of WIPO in connection with International Application No. PCT/US08/071639, on Feb. 2, 2010, 1 page.
Written Opinion, issued by the International Bureau in connection with International Application No. PCT/US08/071639, on Oct. 22, 2008, 4 pages.
International Preliminary Report on Patentability, issued by the International Bureau of WIPO in connection with International Application No. PCT/US08/074467, on Mar. 2, 2010, 1 page.
International Search Report, issued by the International Bureau in connection with International Application No. PCT/US08/074467, on Nov. 17, 2008, 2 pages.
Written Opinion, issued by the International Bureau in connection with International Application No. PCT/US08/074467, on Nov. 17, 2008, 4 pages.
International Preliminary Report of Patentability, issued by the International Bureau in connection with International Application No. PCT/US10/021535, on Jul. 26, 2011, 1 page.
International Search Report, issued by the International Bureau in connection with International Application No. PCT/US10/021535, on Mar. 23, 2010, 3 pages.
Written Opinion, issued by the International Bureau in connection with International Application No. PCT/US10/021535, on Mar. 23, 2010, 4 pages.
International Preliminary Report of Patentability, issued by the International Bureau in connection with International Application No. PCT/US09/065368, on Jun. 23, 2011, 2 pages.
International Search Report, issued by the International Bureau in connection with International Application No. PCT/US09/065368, on Jan. 21, 2010, 3 pages.
Written Opinion, issued by the International Bureau in connection with International Application No. PCT/US09/065368, on Jan. 21, 2010, 7 pages.
International Preliminary Report on Patentability, issued by the International Bureau of WIPO in connection with International Application No. PCT/US08/062275, on Nov. 3, 2009, 1 page.
International Search Report, issued by the International Bureau in connection with International Application No. PCT/US08/071639, on Oct. 22, 2008, 3 pages.
Non-Final Office Action, issued by the United States Patent and Trademark Office in connection with U.S. Appl. No. 13/730,550, on Feb. 20, 2015, 12 pages.
Final Office Action, issued by the United States Patent and Trademark Office in connection with U.S. Appl. No. 12/608,660, on Feb. 20, 2015, 56 pages.
Advisory Action, issued by the United States Patent and Trademark Office in connection with U.S. Appl. No. 12/546,586, on Dec. 22, 2014, 3 pages.
English Translation of Notification of Provisional Rejection, issued by the Korean Patent Office in connection with Patent Application No. 10-2010-7001406, on Oct. 21, 2014, 1 page.
Final Office Action, issued by the United States Patent and Trademark Office in connection with U.S. Appl. No. 12/608,685, on May 5, 2015, 7 pages.
Final Office Action, issued by the United States Patent and Trademark Office in connection with U.S. Appl. No. 13/730,511, on May 6, 2015, 5 pages.
Final Office Action, issued by the United States Patent and Trademark Office in connection with U.S. Appl. No. 13/105,774, on May 14, 2015, 15 pages.
Final Office Action, issued by the United States Patent and Trademark Office in connection with U.S. Appl. No. 12/884,034, on May 14, 2015, 22 pages.
Final Office Action, issued by the United States Patent and Trademark Office in connection with U.S. Appl. No. 13/730,564, on May 22, 2015, 6 pages.
Final Office Action, issued by the United States Patent and Trademark Office in connection with U.S. Appl. No. 13/249,512, on Jun. 30, 2015, 36 pages.
English Translation of Office Action, issued by the Israeli Patent Office in connection with Patent Application No. 201187, on Jun. 22, 2015, 4 pages.
Notification of Provisional Rejection, issued by the Korean Patent Office in connection with Patent Application No. 10-2010-7001406, on Jun. 24, 2015 (with partial translation), 9 pages.
McClure, Samuel, et al., "Neural Correlates of Behavioral Preference for Culturally Familiar Drinks," Neuron (Oct. 14, 2004), 379-387, 9 pages.
Final Office Action, issued by the United States Patent and Trademark Office in connection with U.S. Appl. No. 13/965,805, on Mar. 6, 2015, 18 pages.
Non-Final Office Action, issued by the United States Patent and Trademark Office in connection with U.S. Appl. No. 13/708,344, on Apr. 9, 2015, 12 pages.
Examiner's Answer, issued by the United States Patent and Trademark Office in connection with U.S. Appl. No. 12/113,870, on Jul. 30, 2015, 14 pages.
Examiner's Answer, issued by the United States Patent and Trademark Office in connection with U.S. Appl. No. 12/122,253, on Aug. 4, 2015, 30 pages.
Examiner's Answer, issued by the United States Patent and Trademark Office in connection with U.S. Appl. No. 12/546,586, on Sep. 11, 2015, 7 pages.
Final Office Action, issued by the United States Patent and Trademark Office in connection with U.S. Appl. No. 13/730,550, on Sep. 2, 2015, 5 pages.

(56) References Cited

OTHER PUBLICATIONS

Non-Final Office Action, issued by the United States Patent and Trademark Office in connection with U.S. Appl. No. 12/410,380, on Sep. 10, 2015, 15 pages.
Advisory Action, issued by the United States Patent and Trademark Office in connection with U.S. Appl. No. 12/884,034, on Sep. 16, 2015, 3 pages.
Non-Final Office Action, issued by the United States Patent and Trademark Office in connection with U.S. Appl. No. 13/708,525, on Sep. 30, 2015, 12 pages.
Non-Final Office Action, issued by the United States Patent and Trademark Office in connection with U.S. Appl. No. 13/965,805, on Sep. 30, 2015, 7 pages.
Opitz, S. "Neuromarketing: An Introduction" PowerPoint Presentation (2008), available at http://www.powershow.com/view/94a7b-YzlmN/Neuromarketing_powerpoint_ppt_presentation (last accessed Oct. 14, 2015), 20 pages.
Non-Final Office Action, issued by the United States Patent and Trademark Office in connection with U.S. Appl. No. 13/730,541, on Jul. 23, 2014, 13 pages.
Non-Final Office Action, issued by the United States Patent and Trademark Office in connection with U.S. Appl. No. 13/965,805, on Aug. 6, 2014, 18 pages.
Non-Final Office Action, issued by the United States Patent and Trademark Office in connection with U.S. Appl. No. 13/730,511, on Aug. 13, 2014, 4 pages.
Non-Final Office Action, issued by the United States Patent and Trademark Office in connection with U.S. Appl. No. 13/730,550, on Aug. 14, 2014, 4 pages.
Non-Final Office Action, issued by the United States Patent and Trademark Office in connection with U.S. Appl. No. 13/730,564, on Aug. 15, 2014, 15 pages.
Non-Final Office Action, issued by the United States Patent and Trademark Office in connection with U.S. Appl. No. 12/884,034, on Aug. 21, 2014, 20 pages.
Non-Final Office Action, issued by the United States Patent and Trademark Office in connection with U.S. Appl. No. 12/608,685, on Sep. 4, 2014, 16 pages.
Non-Final Office Action, issued by the United States Patent and Trademark Office in connection with U.S. Appl. No. 13/105,774, on Sep. 18, 2014, 15 pages.
Final Office Action, issued by the United States Patent and Trademark Office in connection with U.S. Appl. No. 12/546,586, on Sep. 24, 2014, 21 pages.
Decision to Grant Patent, issued by the Korean Patent Office in connection with Patent Application No. 10-2009-7022551, on Aug. 13, 2014, 3 pages.
Ekman, P., Friesen, W., Measuring Facial Movement, Environmental Psychology and Nonverbal Behavior, 1 (1) (Fall 1976), pp. 56-75, 20 pages.
Ekman, P., Friesen, W.V., *Facial Action Coding System: A Technique for Measurement of Facial Movement*, Consulting Psychologists Press, Palo Alto, Calif. (1978).
Ekman, P., Friesen, W., *Unmasking the Face—A Guide to Recognizing Emotions from Facial Clues*, Prentice-Hall, Inc., Englewood Cliffs, N.J. (1979).
Ekman, P., Friesen, W., Ancoli, S., Facial Signs of Emotional Experience, J. Personality & Social Psychology, 39(6) (Dec. 1980), pp. 1125-1134, 10 pages.
Izard, C. E., *The Maximally Discriminative Facial Movement Coding System*, (Rev. ed.), Instructional Resources Center, University of Delaware, Newark, Del. (1983).
Izard, C., Dougherty, L., Hembree, E., *A System for Identifying Affect Expressions by Holistic Judgments (AFFEX)*, Instructional Resources Center, University of Delaware, Newark, Del. (1983).
Jia, X., Nixon, M.S., Extending the Feature Set for Automatic Face Recognition, International Conference on Image Processing and Its Applications (Apr. 7-9, 1992), 6 pages.

Lisetti, C., Nasoz, F., Using Noninvasive Wearable Computers to Recognize Human Emotions from Physiological Signals, EURASIP J. Applied Signal Processing, 11 (Sep. 2004), pp. 1672-1687, 16 pages.
Jaimes, A., Sebe, N., Multimodal Human-Computer Interaction: A Survey, Computer Vision and Image Understanding 108 (Oct.-Nov. 2007), pp. 116-134, 19 pages.
Lachaux et al., "Measuring Phase Synchrony in Brain Signals," Human Brain Mapping 8 (1999), 194-208, 15 pages.
Lee et al., "What is 'neuromarketing'? A discussion and agenda for future research," International Journal of Psychophysiology, vol. 63, pp. 199-204, Elsevier (2006), 6 pages.
Lekakos, "Personalized Advertising Services Through Hybrid Recommendation Methods: The Case of Digital Interactive Television," Department of Informatics, Cyprus University, (2004), 11 pages.
Lewis et al., "Market Researchers make Increasing use of Brain Imaging," ACNR, vol. 5, No. 3, pp. 36-37, (Jul./Aug. 2005), 2 pages.
Luck, et al., "The speed of visual attention in schizophrenia: Electrophysiological and behavioral evidence," Schizophrenia Research, pp. 174-195, Elsevier B.V. www.sciencedirect.com, (2006), 22 pages.
Lui et al., "Marketing Strategies in Virtual Worlds," The Data Base for Advances in Information Systems, vol. 38, No. 4, pp. 77-80, (Nov. 2007), 4 pages.
Makeig, et al., "Mining event-related brain dynamics," TRENDS in Cognitive Sciences, vol. 8, No. 5, (May 2004), www.sciencedirect.com, 7 pages.
Makeig, et al., "Dynamic Brain Sources of Visual Evoked Responses," Science, vol. 295, www.sciencemag.org, (Jan. 25, 2002), 5 pages.
The Mathworks, Inc., "MATLAB Data Analysis: Version 7," p. 4-19 (2005), 3 pages.
Miltner, et al., "Coherence of gamma-band EEG activity as a basis for associative learning," Nature, vol. 397, www.nature.com, (Feb. 4, 1999), 3 pages.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
Neurofocus—Neuroscientific Analysis for Audience Engagement, accessed on Jan. 8, 2010 at http://web.archive.org/web/20080621114525/www.neurofocus.com /BrandImage.htm, (2008), 2 pages.
Newell et al., "Categorical perception of familiar objects," Cognition, vol. 85, Issue 2, pp. 113-143 (Sep. 2002), 31 pages.
Nielsen, "Neuroinformatics in Functional Neuroimaging," Informatics and Mathematical Modeling, Technical University of Denmark, (Aug. 30, 2002), 241 pages.
Oberman et al., "EEG evidence for mirror neuron activity during the observation of human and robot actionsAug. 29, 2012 Toward an analysis of the human qualities of interactive robots," Neurocomputing 70 (2007) 2194-2203, 10 pages.
Osborne, "Embedded Watermarking for image Verification in Telemedicine," Thesis submitted for the degree of Doctor of Philosophy, Electrical and Electronic Engineering, University of Adelaide (2005), 219 pages.
Padgett et al., "Categorical Perception in Facial Emotion Classification," In Proceedings of the 18th Annual Conference of the Cognitive Science Society, pp. 249-253 (1996), 5 pages.
Page et al., "Cognitive Neuroscience, Marketing and Research," Congress 2006—Foresight—The Predictive Power of Research Conference Papers, ESOMAR Publications, (Sep. 17, 2006), 25 pages.
Paller, et al., "Validating neural correlates of familiarity," TRENDS in Cognitive Sciences, vol. 11, No. 6, www.sciencedirect.com, (May 2, 2007), 8 pages.
Palva et al., "Phase Synchrony Among Neuronal Oscillations in the Human Cortex," Journal of Neuroscience 25 (2005), 3962-3972, 11 pages.
Picton, et al., "Guidelines for using human event-related potentials to study cognition: Recording standards and publication criteria," Psychophysiology, pp. 127-152, Society for Psychophysiological Research, (2000), 26 pages.

(56) References Cited

OTHER PUBLICATIONS

Rizzolatti et al., "The Mirror-Neuron System," Annu. Rev. Neurosci., vol. 27, pp. 169-192, (Mar. 5, 2004), 30 pages.
Ruchkin et al., "Modality-specific processing streams in verbal working memory: evidence from spatio-temporal patterns of brain activity," Cognitive Brain Research, vol. 6, pp. 95-113, Elsevier, (1997), 19 pages.
Rugg, et al., "Event-related potentials and recognition memory," TRENDS in Cognitive Sciences, vol. 11, No. 6, www.sciencedirect.com, (May 3, 2007), 7 pages.
Rugg, et al., "The ERP and cognitive psychology: conceptual issues," (Sep. 1996), 7 pages.
"User monitoring," Sapien Systems, available at http://web.archive.org/web/20030818043339/http:/www.sapiensystems.com/eyetracking.html, (Aug. 18, 2003), 1 page.
Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.
Spencer, "Averaging, Detection, and Classification of Single-Trial ERPs," in Event-Related Potentials: A Methods Handbook, pp. 209-227, (Todd C. Handy, ed., 2005), 10 pages.
Arousal in Sport, in Encyclopedia of Applied Psychology, vol. 1, p. 159, retrieved from Google Books, (Spielberger, ed., Elsevier Academic Press, 2004), 1 page.
Srinivasan, "High-Resolution EEG: Theory and Practice," in Event-Related Potentials: A Methods Handbook, pp. 167-188, (Todd C. Handy, ed., 2005), 12 pages.
Sullivan et al., "A brain-machine interface using dry-contact, low-noise EEG sensors," In Proceedings of the 2008 IEEE International Symposium on Circuits and Systems, (May 18, 2008), 4 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.
Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.
Taheri, et al., "A dry electrode for EEG recording," Electroencephalography and clinical Neurophysiology, pp. 376-383, Elsevier Science Ireland Ltd. (1994), 8 pages.
Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.
Vogel, et al., "Electrophysiological Evidence for a Postperceptual Locus of Suppression During the Attentional Blink," Journal of Experimental Psychology: Human Perception and Performance, vol. 24, No. 6, pp. 1656-1674 (1998), 19 pages.
Voytek, et al., "Prefrontal cortex and basal ganglia contributions to visual working memory," PNAS Early Edition, www.pnas.org/cgi/doi/10.1073/pnas.1007277107, (2010), 6 pages.
Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, (Nov. 2009) 12 pages.
Wang, "Neurophysiological and Computational Principles of Cortical Rhythms in Cognition," Physiol Rev 90: pp. 1195-1268, American Physiological Society, www.prv.org, (2010), 75 pages.
Anonymous, "Functional magnetic resonance imaging," retrieved online from Wikipedia, the Free Encyclopedia on Aug. 23, 2011, at http://en.wikipedia.org/w/index.php?title=Functional_magnetic_resonance_imaging&oldid=319601772, (Oct. 13, 2009), 8 pages.
William, "Brain Signals to Control Movement of Computer Cursor," Blog article: Brain Signals to Control Movement of Computer Cursor, Artificial Intelligence, retrieved from the Internet on Aug. 17, 2011, http://whatisartificialintelligence.com/899/brain-signals-to-control-movement-of-computer-cursor/, (Feb. 17, 2010), 3 pages.
Woldorf, "Distortion of ERP averages due to overlap from temporally adjacent ERPs: Analysis and correction," Psychophysiology, Society for Psychophysiological Research, Cambridge University Press (1993), 22 pages.
Woodman, et al., "Serial Deployment of Attention During Visual Search," Journal of Experimental Psychology: Human Perception and Performance, vol. 29, No. 1, pp. 121-138, American Physiological Association (2003), 18 pages.
Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.
Yap et al., "TIMER: Tensor Image Morphing for Elastic Registration," NeuroImage, vol. 47, (May 3, 2009), 15 pages.
Yuval-Greenberg, et al., "Transient Induced Gamma-Bands Response in EEG as a Manifestation of Miniature Saccades," Neuron, vol. 58, pp. 429-441, Elsevier Inc. (May 8, 2008), 13 pages.
Ziegenfuss, "Neuromarketing: Advertising Ethical & Medical Technology," The Brownstone Journal, vol. XII, Boston University, pp. 69-73, (May 2005), 5 pages.
Zyga, "A Baseball Cap That Can Read Your Mind," PhysOrg.com, located at www.physorg.com/news130152277.html, (May 16, 2008), 11 pages.
Enghoff, Sigurd, Thesis: "Moving ICA and Time-Frequency Analysis in Event-Related EEG Studies of Selective Attention," Technical University of Denmark, (Dec. 1999), 54 pages.
Zhang, P., "Will You Use Animation on Your Web Pages?" Doing Business on the Internet: Opportunities and Pitfalls, C. Romm and F. Sudweeks (eds.), Spring-Verlag (1999), 17 pages.
Beaver, John D., et al., "Individual Differences in Reward Drive Predict Neural Responses to Images of Food", J. of Neuroscience, (May 10, 2006), 5160-5166, 7 pages.
Tapert, Susan F., et al., "Neural Response to Alcohol Stimuli in Adolescents With Alcohol Use Disorder", Arch Gen Psychiatry (Jul. 2003), 727-735, 9 pages.
Shandlen, Michael N. et al., "A Computational Analysis of the Relationship between Neuronal and Behavioral Responses to Visual Motion", The Journal of Neuroscience, (Feb. 15, 1996) 1486-1510, 25 pages.
Coan et al., "Voluntary Facial Expression and Hemispheric Asymmetry Over the Frontal Cortex," Psycophysiology (Nov. 2001), 912-924, 13 pages.
Aaker et al., "Warmth in Advertising: Measurement, Impact, and Sequence Effects," Journal of Consumer Research, vol. 12, No. 4, pp. 365-381, (Mar. 1986), 17 pages.
Akam, et al., "Oscillations and Filtering Networks Support Flexible Routing of Information," Neuron, vol. 67, pp. 308-320, Elsevier, (Jul. 29, 2010), 13 pages.
Allen et al., "A Method of Removing Imaging Artifact from Continuous EEG Recorded during Functional MRI," Neuroimage, vol. 12, 230-239, (Aug. 2000), 12 pages.
Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.
Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.
Bathe, et al. "Frontal Cortex and the Discovery of Abstract Action Rules," Neuron, vol. 66, pp. 315-326, Elsevier, (Apr. 29, 2010), 13 pages.
Bagozzi et al., "The Role of Emotions in Marketing," Journal of the Academy of Marketing Science, vol. 27, No. 2, pp. 184-206, Academy of Marketing Science (1999), 23 pages.
Barcelo, et al., "Prefrontal modulation of visual processing in humans," Nature Neuroscience, vol. 3, No. 4, Nature America, http//neurosci.nature.com, (Apr. 2000), 5 pages.
Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Belch et al., "Psychophysiological and cognitive Response to Sex in Advertising," Advances in Consumer Research, vol. 9, pp. 424-427, (1982), 6 pages.

(56) References Cited

OTHER PUBLICATIONS

Bimler et al., "Categorical perception of facial expressions of emotion: Evidence from multidimensional scaling," Cognition and Emotion, vol. 15(5), pp. 633-658 (Sep. 2001), 26 pages.

Blakeslee, "If You Have a 'Buy Button' in Your Brain, What Pushes It?" The New York Times, www.nytimes.com, (Oct. 19, 2004), 3 pages.

Braeutigam, "Neuroeconomics—From neural systems to economic behavior," Brain Research Bulletin, vol. 67, pp. 355-360, Elsevier, (2005), 6 pages.

Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.

Buschman, et al., "Serial, Covert Shifts of Attention during Visual Search Are Reflected by the Frontal Eye Fields and Correlated with Population Oscillations," Neuron, vol. 63, pp. 386-396, Elsevier, (Aug. 13, 2009), 11 pages.

Canolty, et al., "High Gamma Power is Phase-Locked to Theta Oscillations in Human Neocortex," Science, vol. 313, www.sciencemag.org, (Sep. 15, 2006), 3 pages.

Cheng, et al. "Gender Differences in the Mu Rhythm of the Human Mirror-Neuron System," PLos ONE, vol. 3, Issue 5, www.plosone.org, (May 2008), 7 pages.

Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, (Mar. 28, 2007), 8 pages.

Clifford, "Billboards That Look Back," The New York Times, NYTimes.com, available at http://www.nytimes.com/2008/05/31/business/media/31billboard.html, (May 31, 2008), 4 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

Davidson, et al., "The functional neuroanatomy of emotion and affective style," TRENDS in Cognitive Sciences, vol. 3, No. 1, (Jan. 1999), 11 pages.

de Gelder et al., "Categorical Perception of Facial Expressions: Categories and their Internal Structure," Cognition and Emotion, vol. 11(1), pp. 1-23 (1997), 23 pages.

D'Esposito, "From cognitive to neural models of working memory," Phil. Trans. R. Soc. B, doi: 10.1098/rstb.2007.2086, (Mar. 30, 2007), 12 pages.

Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.

Dien, et al., "Application of Repeated Measures ANOVA to High-Dens Dataset: A Review and Tutorial," in Event-Related Potentials: A Methods Handbook pp. 57-82, (Todd C. Handy, ed., 2005), 14 pages.

Edgar, et al., "Digital Filters in ERP Research," in Event-Related Potentials: A Methods Handbook pp. 85-113, (Todd C. Handy, ed., 2005), 15 pages.

EEG Protocols, "Protocols for EEG Recording," retrieved from the Internet on Aug. 23, 2011, http://www.q-metrx.com/EEGrecordingProtocols.pdf, (Nov. 13, 2007), 3 pages.

Engel et al., "Dynamic Predictions: Oscillations and Synchrony in Top-down Processing," Nature Reviews: Neuroscience, vol. 2, pp. 704-716, Macmillian Magazines Ltd., (Oct. 2001), 13 pages.

Filler, "MR Neurography and Diffusion Tensor Imaging: Origins, History & Clinical Impact of the first 50,000 Cases With an Assortment of Efficacy and Utility in a Prospective 5,000 Patent Study Group," Institute for Nerve Medicine, (Nov. 7, 2008), 56 pages.

Flinker, A. et al, "Sub-centimeter language organization in the human temporal lobe," Brain and Language, Elsevier Inc., (2010), doi.org/10.1016/j.bandl.2010.09.009, 7 pages.

Fogelson, et al., "Prefrontal cortex is critical for contextual processing: evidence from brain lesions," Brain: A Journal of Neurology, vol. 132, pp. 3002-3010, doi:10.1093/brain/awp230, (Aug. 27, 2009), 9 pages.

Friedman, et al., "Event-Related Potential (ERP) Studies of Memory Encoding and Retrieval: A Selective Review," Microscopy Research and Technique 51:6-26, Wiley-Less, Inc. (2000), 23 pages.

Fries, "A mechanism for cognitive dynamics: neuronal coherence," Trends in Cognitive Sciences, vol. 9, No. 10, pp. 474-480, Elsevier B.V. www.sciencedirect.com, (Oct. 2005), 7 pages.

Fuster, "Cortex and Memory: Emergence of a New Paradigm," Journal of Cognitive Neuroscience, vol. 21, No. 11, pp. 2047-2072, Massachusetts Institute of Technology, (Nov. 2009), 26 pages.

Gaillard, "Problems and Paradigms in ERP Research," Biological Psychology, Elsevier Science Publisher B.V. (1988), 10 pages.

Gargiulo et al., "A Mobile EEG System With Dry Electrodes," (Nov. 2008), 4 pages.

Gazzaley et al., "Top-down Enhancement and Suppression of Magnitude and Speed of Neural Activity," Journal of Cognitive Neuroscience, vol. 17, No. 3, pp. 507-517, Massachusetts Institute of Technology, (2005), 11 pages.

Griss et al., "Characterization of micromachined spiked biopotential electrodes", Biomedical Engineering, IEEE Transactions (Jun. 2002), 8 pages.

Haq, "This is Your Brain on Advertising," Business Week, Market Research, (Oct. 8, 2007), 3 pages.

Hartikainen et al., Manuscript Draft of "Emotionally arousing stimuli compete with attention to left hemispace," NeuroReport, (Sep. 8, 2007), 26 pages.

Hazlett, et al., "Emotional Response to Television Commercials: Facial EMG vs. Self-Report," Journal of Advertising Research, (Apr. 1999), 17 pages.

Herrmann, et al., "Mechanisms of human attention: event-related potentials and oscillations," Neuroscience and Biobehavioral Reviews, pp. 465-476, Elsevier Science Ltd., www.elsvevier.com/locate/neubiorev, (2001), 12 pages.

Hopf, et al., "Neural Sources of Focused Attention in Visual Search," Cerebral Cortex, 10:1233-1241, Oxford University Press, (Dec. 2000), 9 pages.

Jung et al., "Analysis and Visualization of Single-Trial Event-Related Potentials," Human Brain Mapping vol. 14, 166-185 (2001), 20 pages.

Kay et al., "Identifying natural images from human brain activity," Nature, vol. 452, pp. 352-356, Nature Publishing Group, (Mar. 20, 2008), 5 pages.

Keren, et al., "Saccadic spike potentials in gamma-band EEG: Characterization, detection and suppression," NeuroImage, http://dx.doi:10.1016/j.neuroimage.2009.10.057, (Oct. 2009), 16 pages.

Kishiyama, et al., "Novelty Enhancements in Memory Are Dependent on Lateral Prefrontal Cortex," The Journal of Neuroscience, pp. 8114-8118, Society for Neuroscience (Jun. 24, 2009), 5 pages.

Kishiyama, et al., "Socioeconomic Disparities Affect Prefrontal Function in Children," Journal of Cognitive Neuroscience pp. 1106-1115, Massachusetts Institute of Technology, (2008), 10 pages.

Klimesch, "EEG alpha and theta oscillations reflect cognitive and memory performance a review and analysis," Brain Research Reviews, vol. 29, 169-195, (1999), 27 pages.

Knight, "Contribution of human hippocampal region to novelty detection," Nature, vol. 383, www.nature.com, (Sep. 19, 1996), 4 pages.

Knight, "Consciousness Unchained: Ethical Issues and the Vegetative and minimally Conscious State," The American Journal of Bioethics, 8:9, 1-2, http://dx.doi.org/10.1080/15265160802414524, (Sep. 1, 2008), 3 pages.

Knight, et al., "Prefrontal cortex regulates inhibition and excitation in distributed neural networks," Acta Psychologica vol. 101, pp. 159-178, Elsevier (1999), 20 pages.

Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.

(56) References Cited

OTHER PUBLICATIONS

Krakow et al., "Methodology: EEG-correlated fMRI," Functional Imaging in the Epilepsies, (Lippincott Williams & Wilkins, 2000), 17 pages.

Krugman, "Brain Wave Measures of Media Involvement," Journal of Advertising Research vol. 11, 3-9 (Feb. 1971), 7 pages.

Duchowski, "A Breadth-First Survey of Eye-tracking Applications," Beahavior Research Methods, Instruments, and Computers (Nov. 2002), 455-470, 16 pages.

Heo et al., "Wait! Why is it Not Moving? Attractive and Distractive Ocular Responses to Web Ads," Paper presented to AEJMC, (Aug. 2001) Washington, DC, available at.

Rothschild et al., "Predicting Memory for Components of TV Commercials from EEG," Journal of Consumer Research (Mar. 1990), p. 472-478, 9 pages.

"Final Office Action," issued by the United States Patent and Trademark Office in connection with U.S. Appl. No. 13/708,344, on Nov. 20, 2015, 18 pages.

"Examiner's Answer," issued by the United States Patent and Trademark Office in connection with U.S. Appl. No. 13/730,541, on Dec. 18, 2015, 7 pages.

"Non-Final Office Action," issued by the United States Patent and Trademark Office in connection with U.S. Appl. No. 12/608,685, on Dec. 17, 2015, 16 pages.

"Translation of Reexamination Decision," issued by the Chinese Patent Office in connection with Patent Application No. 200880017883.X, on Nov. 13, 2015, 1 page.

Non-Final Office Action, issued by the United States Patent and Trademark Office in connection with U.S. Appl. No. 12/608,660, on Jan. 22, 2016, 38 pages.

Final Office Action, issued by the United States Patent and Trademark Office in connection with U.S. Appl. No. 13/708,525, on Feb. 3, 2016, 22 pages.

Examiner's Answer, issued by the United States Patent and Trademark Office in connection with U.S. Appl. No. 13/730,511, on Feb. 18, 2016, 5 pages.

Non-Final Office Action, issued by the United States Patent and Trademark Office in connection with U.S. Appl. No. 12/410,372, on Feb. 23, 2016, 24 pages.

Final Office Action, issued by the United States Patent and Trademark Office in connection with U.S. Appl. No. 12/410,380, on Mar. 22, 2016, 27 pages.

English Translation of Notification of Provisional Rejection, issued by the Korean Patent Office in connection with Patent Application No. 10-2010-7001406, on Jan. 26, 2016, 1 page.

English Translation of Notification to Grant Patent Right for Invention, issued by the State Intellectual Property Office of P.R. China in connection with Patent Application No. 200880017883.X, on Feb. 3, 2016, 2 pages.

Landau et al., "Different Effects of Voluntary and Involunatly Attention on EEG Activity in the Gamma Band," J of Neuroscience 27(44), Oct. 31, 2007, pp. 11986-11990, 5 pages.

* cited by examiner

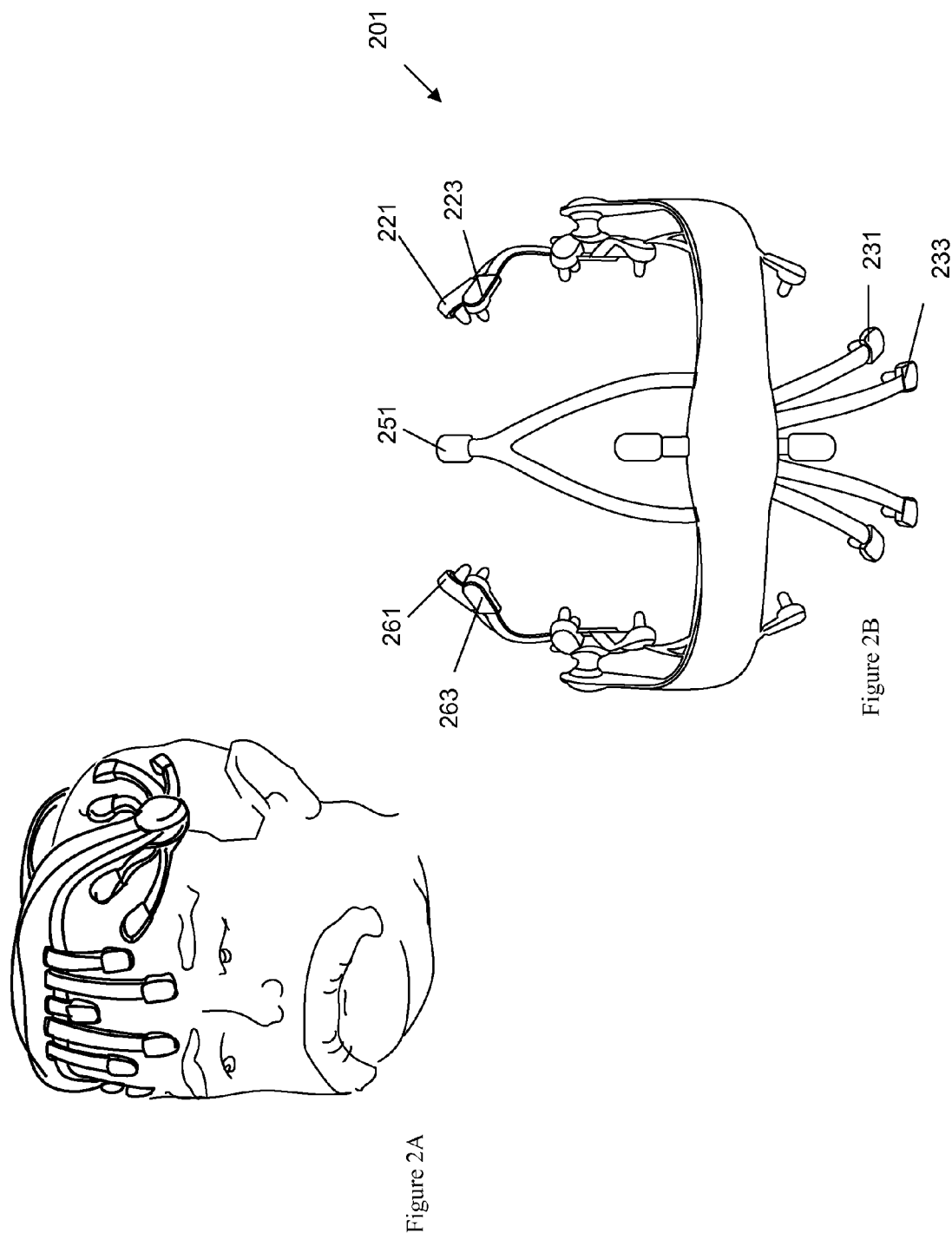

| Dataset Data Model 301 | | | | |
|---|---|---|---|---|
| Experiment Name 303 | Client Attributes 305 | Subject Pool 307 | Logistics Information 309 | Stimulus Material 311 | ... |

| Subject Attributes Data Model 315 | | | |
|---|---|---|---|
| Subject Name 317 | Demographic Attributes 319 | Contact Information 321 | ... |

| Data Collection Data Model 337 | | | |
|---|---|---|---|
| Recording Attributes 339 | Equipment Attributes 341 | Modalities Recorded 343 | Data Storage Attributes 345 | ... |

| Preset Query Data Model 349 | | | |
|---|---|---|---|
| Query Name 351 | Accessed Data Collection 353 | Access Security Attributes 355 | Refresh Attributes 357 |

Figure 3

| Subject Attributes Queries 415 | | | |
|---|---|---|---|
| Location 417 | Demographic Attributes 419 | Time Information 421 | Location Information 423 ... |

| Response Assessment Queries 437 | | | |
|---|---|---|---|
| Attention Score 439 | Emotion Score 441 | Retention Score 443 | Effectiveness Score 445 ... |

Figure 4

| Client Assessment Summary Reports 501 | | |
|---|---|---|
| Effectiveness 503 | Component Assessment 505 | Distributed Neuro-Response Data Collection 507 | ... |

| Client Cumulative Reports 511 | | |
|---|---|---|
| Media Grouped 513 | Campaign Grouped 515 | Time/Location Grouped 517 | ... |

| Industry Cumulative And Syndicated Reports 521 | | | |
|---|---|---|---|
| Aggregate Assessment 523 | Top Performers 525 | Bottom Performers 527 | Outliers 529 | Trend 531 | ... |

Figure 5

NEURO-RESPONSE DATA SYNCHRONIZATION

RELATED APPLICATIONS

This patent arises from a continuation of U.S. patent application Ser. No. 12/778,828, now U.S. Pat. No. 8,655,428, which is entitled "Neuro-Response Data Synchronization," filed on May 12, 2010, and is hereby incorporated by reference in its entirety.

This patent is related to U.S. patent application Ser. No. 12/056,190; U.S. patent application Ser. No. 12/056,211; U.S. patent application Ser. No. 12/056,221; U.S. patent application Ser. No. 12/056,225; U.S. patent application Ser. No. 12/113,863; U.S. patent application Ser. No. 12/113,870; U.S. patent application Ser. No. 12/122,240; U.S. patent application Ser. No. 12/122,253; U.S. patent application Ser. No. 12/122,262; U.S. patent application Ser. No. 12/135,066; U.S. patent application Ser. No. 12/135,074; U.S. patent application Ser. No. 12/182,851; U.S. patent application Ser. No. 12/182,874; U.S. patent application Ser. No. 12/199,557; U.S. patent application Ser. No. 12/199,583; U.S. patent application Ser. No. 12/199,596; U.S. patent application Ser. No. 12/200,813; U.S. patent application Ser. No. 12/234,372; U.S. patent application Ser. No. 12/135,069; U.S. patent application Ser. No. 12/234,388; U.S. patent application Ser. No. 12/544,921; U.S. patent application Ser. No. 12/544,934; U.S. patent application Ser. No. 12/546,586; U.S. patent application Ser. No. 12/544,958; U.S. patent application Ser. No. 12/846,242; U.S. patent application Ser. No. 12/410,380; U.S. patent application Ser. No. 12/410,372; U.S. patent application Ser. No. 12/413,297; U.S. patent application Ser. No. 12/545,455; U.S. patent application Ser. No. 12/608,660; U.S. patent application Ser. No. 12/608,685; U.S. patent application Ser. No. 13/444,149; U.S. patent application Ser. No. 12/608,696; U.S. patent application Ser. No. 12/731,868; U.S. patent application Ser. No. 13/045,457; U.S. patent application Ser. No. 12/778,810; U.S. patent application Ser. No. 13/104,821; U.S. patent application Ser. No. 13/104,840; U.S. patent application Ser. No. 12/853,197; U.S. patent application Ser. No. 12/884,034; U.S. patent application Ser. No. 12/868,531; U.S. patent application Ser. No. 12/913,102; U.S. patent application Ser. No. 12/853,213; and U.S. patent application Ser. No. 13/105,774.

TECHNICAL FIELD

The present disclosure relates to portable electroencephalography (EEG) headsets and stimulus synchronization.

BACKGROUND

Conventional electroencephalography (EEG) systems use scalp level electrodes typically attached to elastic caps or bands to monitor neurological activity. Conductive gels and pastes are applied before placement of the scalp electrodes to improve sensitivity. However, application of conductive gels and pastes is often inconvenient and time consuming. Furthermore, conductive gels and pastes can often bleed between neighboring electrodes and cause signal contamination. Elastic caps or bands can also be uncomfortable for prolonged use. Conventional mechanisms are often used in highly controlled laboratory environments under supervision of trained technicians.

Some efforts have been made in the development of more portable, efficient, and effective EEG data collection mechanisms. However, available mechanisms have a variety of limitations. Consequently, it is desirable to provide improved mechanisms for collecting EEG data.

BRIEF DESCRIPTION OF THE DRAWINGS

The disclosure may best be understood by reference to the following description taken in conjunction with the accompanying drawings, which illustrate particular examples.

FIGS. 2A-2E illustrate a particular example of a neuro-response data collection mechanism. In the examples shown, the example neuro-response data collection mechanism includes electrodes connected to hubs on the sides of the data collection mechanism, which are rotatable, for example, between the position shown in FIG. 2C and the position shown in FIG. 2E.

FIG. 3 illustrates examples of data models that can be used with a stimulus and response repository.

FIG. 4 illustrates one example of a query that can be used with the neuro-response collection system.

FIG. 5 illustrates one example of a report generated using the neuro-response collection system.

DETAILED DESCRIPTION

Figure 1:
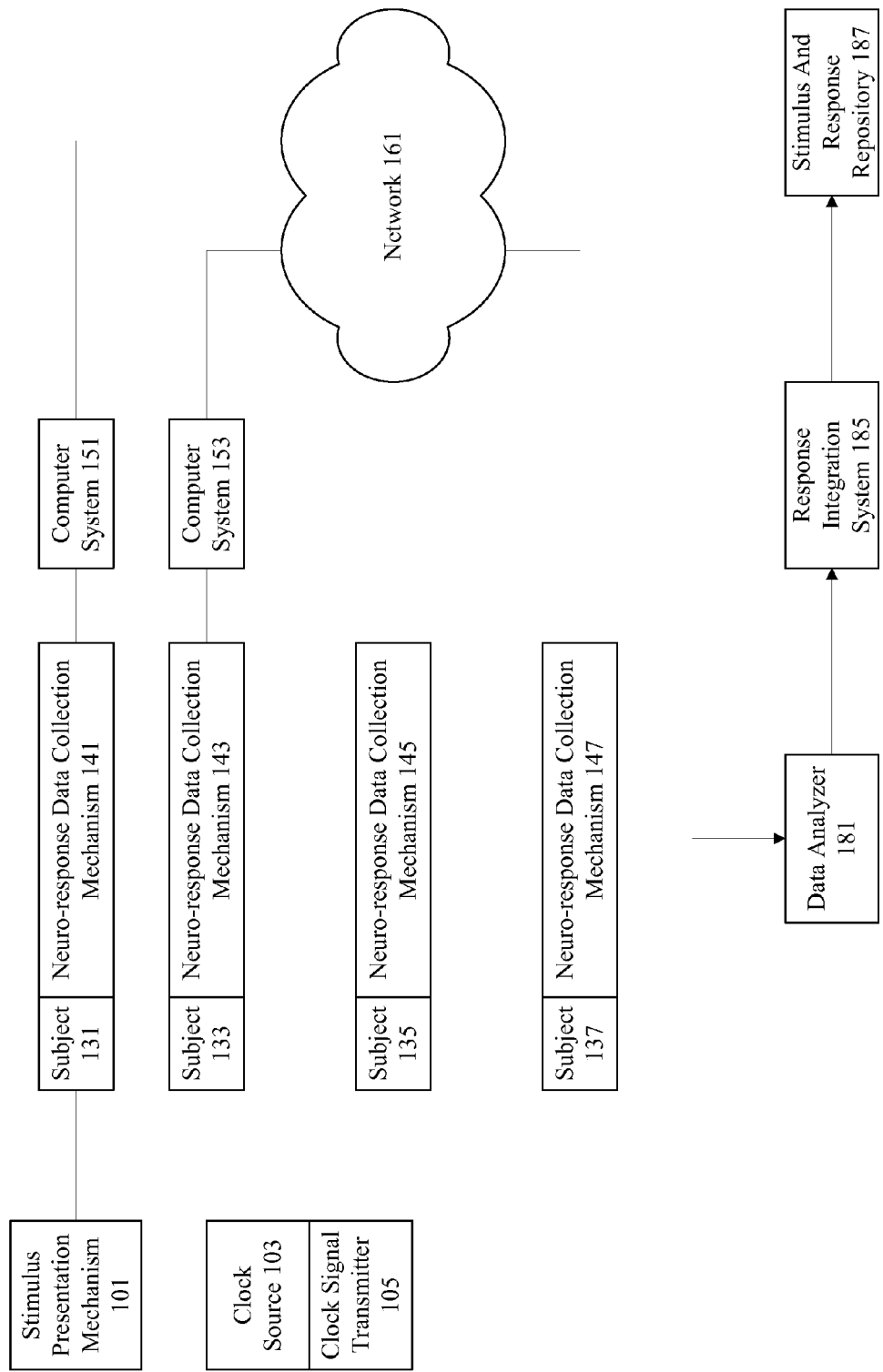
FIG. 1 illustrates one example of a system for performing neuro-response data synchronization.

Reference will now be made in detail to some specific examples constructed in accordance with the teachings of the invention including the best modes contemplated by the inventors for carrying out the examples disclosed herein. Specific examples are illustrated in the accompanying drawings. It is not intended to limit the teachings of this disclosure to the described examples. On the contrary, it is intended to cover alternatives, modifications, and equivalents as may be included within the spirit and scope of the teachings of this disclosure as defined by the claims.

Example techniques and mechanisms disclosed herein will be described in the context of particular types of electrodes. However, it should be noted that example techniques and mechanisms of the present disclosure apply to a variety of different types of electrodes and contacts. In the following description, numerous specific details are set forth in order to provide a thorough understanding of the present examples. Some examples may be implemented without some or all of these specific details. In other instances, well known process operations have not been described in detail in order not to unnecessarily obscure the teachings of this disclosure.

Some example techniques and mechanisms will sometimes be described in singular form for clarity. However, it should be noted that some examples include multiple iterations of a technique or multiple instantiations of a mechanism unless noted otherwise. For example, a system uses a processor in a variety of contexts. However, it will be appreciated that a system can use multiple processors while remaining within the scope of the present disclosure unless otherwise noted. Furthermore, the example techniques and mechanisms of the present disclosure will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

Efficient and effective mechanisms for collecting electroencephalography (EEG) data are provided to synchronize neuro-response data collection with stimulus material presentation for in situ engagement monitoring and tracking. An EEG headset includes multiple point electrodes individually isolated and amplified. In some examples, a stimulus material presentation mechanism includes a clock source and a clock transmitter. The clock transmitter sends clock signals to a neuro-response data collection mechanism to allow synchronization of neuro-response data collected with stimulus presentation events. The EEG headset can be configured to perform processing while supporting both continuous input and output.

EXAMPLES

Conventional distributed response monitoring mechanisms merely track stimulus being viewed and rely on behavior and survey based data collected from subjects exposed to stimulus materials. In some instances, attempts are made to measure responses to programs and commercials using demographic, statistical, user behavioral, and survey based information. For example, subjects are required to complete surveys after exposure to programs and/or commercials. However, survey results often provide only limited information about program and commercial response. For example, survey subjects may be unable or unwilling to express their true thoughts and feelings about a topic, or questions may be phrased with built in bias. Articulate subjects may be given more weight than non-expressive ones. Analysis of multiple survey responses and correlation of the responses to stimulus material is also limited. A variety of semantic, syntactic, metaphorical, cultural, social and interpretive biases and errors prevent accurate and repeatable evaluation. Mechanisms for storing, managing, and retrieving conventional responses are also limited.

Consequently, example techniques and mechanisms of the present disclosure use EEG measurements to allow more accurate measurement and monitoring of attention and engagement. According to some examples, an EEG headset is provided to subjects for use home, recreational, work, as well as laboratory environments. In some examples, the EEG headset includes multiple dry electrodes individually isolated and amplified. Data from individual electrodes may be processed prior to continuous transmission to a data analyzer. Processing may include filtering to remove noise and artifacts as well as compression and/or encryption. Individual electrodes are configured to contact the scalp in a variety of areas while avoiding the contact with the temporal region.

According to some examples, an electric cap or band is not required because individual opposing electrodes are attached to exert somewhat opposing forces to secure a headset. In some examples, a headset spring mechanism exerts elastic forces to push both frontal and rear electrodes into close contact with the scalp. According to some examples, frontal electrodes exert point forces that counterbalance point forces exerted by rear electrodes. Electrodes are shaped as points to reach the scalp through non-conductive hair follicles. One of more elastic mechanisms can be used to allow for effective counterbalancing forces. In some examples, right side scalp electrodes counterbalance forces from left side scalp electrodes to secure a headset, allowing front electrodes and rear electrodes to contact the scalp. It should be noted that forces need not perfectly counterbalance.

EEG dry electrodes allow in situ monitor and tracking of neuro-response activity including engagement levels. According to some examples, the data collection mechanism is synchronized with stimulus material to allow determination of aspects of stimulus materials that evoke particular neurological responses. In some examples, the EEG headset is synchronized with stimulus data using a shared clock or an external clock from a cell tower or a satellite. Although a headset may merely have an internal clock that generates timestamps, it is recognized that timestamps in themselves are insufficient to provide for the precise measurements used to determine subject neurological responses.

According to some examples, a stimulus material presentation mechanism uses a clock source to transmit clock signals to an EEG headset. The clock source may be an external clock, timing information embedded in a stimulus material presentation stream, a device clock, etc. In some examples, the EEG headset stores neuro-response data collected from a user exposed to stimulus material for transmission to a data analyzer. Neuro-response data is synchronized with timing information associated with the stimulus material presentation to allow identification of responses and associated events in the neuro-response data. In some examples, neuro-response data is stored with synchronized timing data to allow placement of stimulus material and neuro-response data on the same time scale.

According to some examples, the EEG headset uses flexible printed circuit boards (PCBs) to enhance shielding, routability and connectability of elements including amplifiers, sensors, transmitters, etc.

A subject may wear the portable neuro-response data collection mechanism during a variety of activities in non-laboratory settings. This allows collection of data from a variety of sources while a subject is in a natural state. In some examples, data collection can occur effectively in corporate and laboratory settings, but it is recognized that neuro-response data may even be more accurate if collected while a subject is in a more natural environment.

A variety of neurological, neuro-physiological, and effector mechanisms may be integrated in a neuro-response data collection mechanism. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly. Portable EEG with dry electrodes provide a large amount of neuro-response information. It should be recognized that other mechanisms such as Electrooculography (EOG), eye tracking, facial emotion encoding, reaction time, Functional Magnetic Resonance Imaging (fMRI) and Magnetoencephalography (MEG) can also be used in some examples.

According to some examples, the techniques and mechanisms of the present disclosure intelligently blend multiple modes and manifestations of precognitive neural signatures with cognitive neural signatures and post cognitive neurophysiological manifestations to more accurately allow monitoring.

According to some examples, subjects may be exposed to predetermined or preselected stimulus material. In other examples, no predetermined or preselected stimulus material is provided and a system collects neuro-response data for stimulus material a user is exposed to during typical activities.

For example, multiple subjects may be provided with portable EEG monitoring systems with dry electrodes that allow monitoring of neuro-response activity while subjects view billboards. Response data is analyzed and integrated. In some examples, all response data is provided for data analysis. In other examples, interesting response data along with recorded stimulus material is provided to a data analyzer. According to some examples, response data is analyzed and enhanced for each subject and further analyzed and enhanced by integrating data across multiple subjects.

According to some examples, individual and integrated response data is numerically maintained or graphically represented. Measurements for multiple subjects are analyzed to determine possible patterns, fluctuations, profiles, etc.

According to some examples, neuro-response data may show particular effectiveness of stimulus material for a particular subset of individuals. A variety of stimulus materials such as entertainment and marketing materials, media streams, billboards, print advertisements, text streams, music, performances, sensory experiences, etc. can be analyzed. According to some examples, enhanced neuro-response data is generated using a data analyzer that performs both intra-modality measurement enhancements and cross-modality measurement enhancements. According to some examples, brain activity is measured not just to determine the regions of activity, but to determine interactions and types of interactions between various regions. The example techniques and mechanisms of the present disclosure recognize that interactions between neural regions support orchestrated and organized behavior. Attention, emotion, memory, retention, priming, and other characteristics are not merely based on one part of the brain but instead rely on network interactions between brain regions.

Example techniques and mechanisms of the present disclosure further recognize that different frequency bands used for multi-regional communication can be indicative of the effectiveness of stimuli. In some examples, evaluations are calibrated to each subject and synchronized across subjects. In some examples, templates are created for subjects to create a baseline for measuring pre and post stimulus differentials. According to some examples, stimulus generators are intelligent and adaptively modify specific parameters such as exposure length and duration for each subject being analyzed.

FIG. 1 illustrates one example of a system for collection of neuro-response data. Subjects 131, 133, 135, and 137 are associated with neuro-response data collection mechanisms 141, 143, 145, and 147. According to some examples, subjects voluntarily use neuro-response data collection mechanisms such as EEG caps, EOG sensors, recorders, cameras, etc., during exposure to particular stimulus materials provided by stimulus presentation mechanism 101 or during normal activities in non-laboratory environments. According to some examples, neuro-response data is measured for subjects in non-laboratory settings including homes, shops, workplaces, parks, theatres, etc. In some examples, neuro-response data collection mechanisms 145 and 147 include persistent storage mechanisms and network 161 interfaces that are used to transmit collected data to a data analyzer 181. In other examples, neuro-response data collection mechanisms 141 and 143 include interfaces to computer systems 151 and 153 that are configured to transmit data to a data analyzer 181 over one or more networks. According to some examples, stimulus material is clock synchronized with the data collection mechanisms 141, 143, 145, and 147. In some examples, stimulus material presentation mechanism 101 and the data collection mechanisms 141, 143, 145, and 147 are clock synchronized using a clock source 103 and a clock signal transmitter 105. The clock source 103 may be timing information embedded in stimulus material, a cell tower or satellite clock signal, a stimulus presentation device clock, a EEG headset clock, etc. A clock signal transmitter 105 may be a transmitter associated with the stimulus material presentation mechanism 101, a transmitter associated with the EEG headset, a cell tower or satellite, etc. According to some examples, the stimulus material presentation mechanism 101 and data collection mechanisms 141, 143, 145, and 147 also have clock signal receivers.

Materials eliciting neuro-responses from subjects 131, 133, 135, and 137 may include people, activities, brand images, information, performances, entertainment, advertising, and may involve particular tastes, smells, sights, textures and/or sounds. In some examples, stimulus material is selected for presentation to subjects 131, 133, 135, and 137. In other examples, stimulus material subjects are exposed to during normal everyday activities such as driving to work or going to the grocery store are analyzed. Continuous and discrete modes are supported.

According to some examples, the subjects 131, 133, 135, and 137 are connected to neuro-response data collection mechanisms 141, 143, 145, and 147. The data collection mechanisms 105 includes EEG electrodes, although in some implementations may also include a variety of neuro-response measurement mechanisms including neurological and neurophysiological measurements systems such as EOG, GSR, EKG, pupillary dilation, eye tracking, facial emotion encoding, and reaction time devices, etc. According to some examples, neuro-response data includes central nervous system, autonomic nervous system, and/or effector data.

The neuro-response data collection mechanisms 141, 143, 145, and 147 collect neuro-response data from multiple sources. According to some examples, data collection mechanisms include central nervous system sources (EEG), autonomic nervous system sources (EKG, pupillary dilation), and effector sources (EOG, eye tracking, facial emotion encoding, reaction time). In some examples, data collected is digitally sampled and stored for later analysis. In some examples, the data collected can be analyzed in real-time. According to some examples, the digital sampling rates are adaptively chosen based on the neurophysiological and neurological data being measured.

In an example, the neuro-response data collection mechanism includes EEG measurements made using scalp level electrodes, EOG measurements made using shielded electrodes to track eye data, and a facial affect graphic and video analyzer adaptively derived for each individual.

In some examples, the data collection mechanisms 141, 143, 145, and 147 also include a condition evaluation subsystem that provides auto triggers, alerts and status monitoring and visualization components that continuously monitor the status of the subject, the direction of attention, stimulus being presented, data being collected, and the data collection instruments. For example, the data collection mechanisms may record neuro-response data while a recorder determines that a subject is listening to a particular song.

The condition evaluation subsystem may also present visual alerts and automatically trigger remedial actions. According to some examples, the data collection devices include mechanisms for not only monitoring subject neuro-response to stimulus materials, but also include mechanisms for identifying and monitoring the stimulus materials. For example, data collection mechanisms 105 may be synchronized with a set-top box to monitor channel changes. In other examples, data collection mechanisms 105 may be directionally synchronized to monitor when a subject is no longer paying attention to stimulus material. In still other examples, the data collection mechanisms 105 may receive and store stimulus material generally being viewed by the subject, whether the stimulus is a program, a commercial, printed material, or a scene outside a window of a living room. The data collected allows analysis of neuro-response information and correlation of the information to actual stimulus material and not mere subject distractions.

According to some examples, the neuro-response collection system also includes a data cleanser. In some examples, the data cleanser device filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject, e.g. a phone ringing while a subject is viewing a video) and endogenous artifacts (where the source could be neurophysiological, e.g. muscle movements, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to some examples, the data cleanser device is implemented using hardware, firmware, and/or software and may be integrated into EEG headsets, computer systems, or data analyzers. It should be noted that although a data cleanser device may have a location and functionality that varies based on system implementation.

The data cleanser can pass data to the data analyzer 181. The data analyzer 181 uses a variety of mechanisms to analyze underlying data in the system to determine neuro-response characteristics associated with corresponding stimulus material. According to some examples, the data analyzer customizes and extracts the independent neurological and neuro-physiological parameters for each individual in each modality, and blends the estimates within a modality as well as across modalities to elicit an enhanced response to the stimulus material. In some examples, stimulus material recorded using images, video, or audio is synchronized with neuro-response data. In some examples, the data analyzer 181 aggregates the response measures across subjects in a dataset.

According to some examples, neurological and neuro-physiological signatures are measured using time domain analyses and frequency domain analyses. Such analyses use parameters that are common across individuals as well as parameters that are unique to each individual. The analyses could also include statistical parameter extraction and fuzzy logic based attribute estimation from both the time and frequency components of the synthesized response.

In some examples, statistical parameters used in a blended effectiveness estimate include evaluations of skew, peaks, first and second moments, population distribution, as well as fuzzy estimates of attention, emotional engagement and memory retention responses.

According to some examples, the data analyzer 181 may include an intra-modality response synthesizer and a cross-modality response synthesizer. In some examples, the intra-modality response synthesizer is configured to customize and extract the independent neurological and neurophysiological parameters for each individual in each modality and blend the estimates within a modality analytically to elicit an enhanced response to the presented stimuli. In some examples, the intra-modality response synthesizer also aggregates data from different subjects in a dataset.

According to some examples, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to some examples, the data analyzer 181 also includes a composite enhanced effectiveness estimator (CEEE) that combines the enhanced responses and estimates from each modality to provide a blended estimate of the effectiveness. In some examples, blended estimates are provided for each exposure of a subject to stimulus materials. According to some examples, numerical values are assigned to each blended estimate. The numerical values may correspond to the intensity of neuro-response measurements, the significance of peaks, the change between peaks, etc. Higher numerical values may correspond to higher significance in neuro-response intensity. Lower numerical values may correspond to lower significance or even insignificant neuro-response activity. In other examples, multiple values are assigned to each blended estimate. In still other examples, blended estimates of neuro-response significance are graphically represented to show changes after repeated exposure.

According to some examples, the data analyzer 181 provides analyzed and enhanced response data to a response integration system 185. According to some examples, the response integration system 185 combines analyzed and enhanced responses to the stimulus material while using information about stimulus material attributes. In some examples, the response integration system 185 also collects and integrates user behavioral and survey responses with the analyzed and enhanced response data to more effectively measure and neuro-response data collected in a distributed environment.

According to some examples, the response integration system 185 obtains characteristics of stimulus material such as requirements and purposes of the stimulus material. Some of these requirements and purposes may be obtained from a stimulus attribute repository. Others may be obtained from other sources. Characteristics may include views and presentation specific attributes such as audio, video, imagery and messages needed, media for enhancement, media for avoidance, etc.

According to some examples, the response integration system 185 also includes mechanisms for the collection and storage of demographic, statistical and/or survey based responses to different entertainment, marketing, advertising and other audio/visual/tactile/olfactory material. If this information is stored externally, the response integration system 185 can include a mechanism for the push and/or pull integration of the data, such as querying, extraction, recording, modification, and/or updating.

According to some examples, the response integration system 185 integrates the requirements for the presented material, the assessed neuro-physiological and neuro-behavioral response measures, and the additional stimulus attributes such as demographic/statistical/survey based responses into a synthesized measure for various stimulus material consumed by users in various environments.

According to some examples, the response integration system 185 provides stimulus and response repository 187 with data including integrated and/or individual stimulus material responses, stimulus attributes, synthesized measures, stimulus material, etc. A variety of data can be stored for later analysis, management, manipulation, and retrieval. In some examples, the repository 187 could be used for tracking stimulus attributes and presentation attributes, audience responses and optionally could also be used to integrate audience measurement information.

According to some examples, the information stored in the repository system 187 could be used to assess the audience response to programs/advertisements in multiple regions, across multiple demographics and multiple time spans (days, weeks, months, years, etc.), determine the effectiveness of billboards, monitor neuro-responses to video games and entertainment, etc.

As with a variety of the components in the neuro-response collection system, the response integration system can be co-located with the rest of the system and the user, or could be implemented in a remote location. It could also be optionally separated into an assessment repository system that could be centralized or distributed at the provider or providers of the stimulus material. In other examples, the response integration system is housed at the facilities of a third party service provider accessible by stimulus material providers and/or users.

Figure 2D:
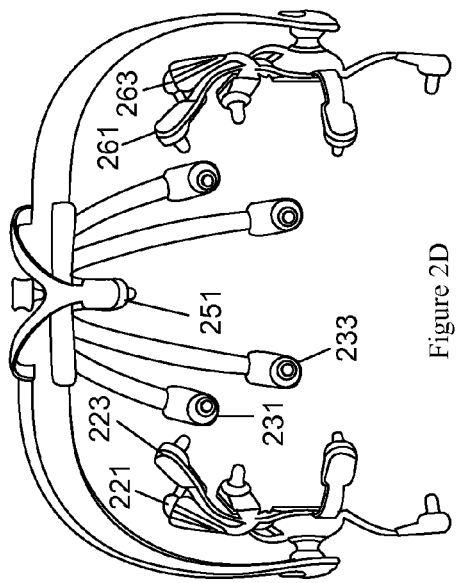
Figure 2E:
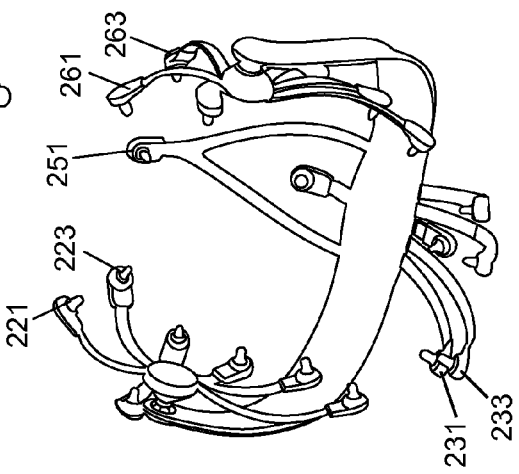
Figure 2C:
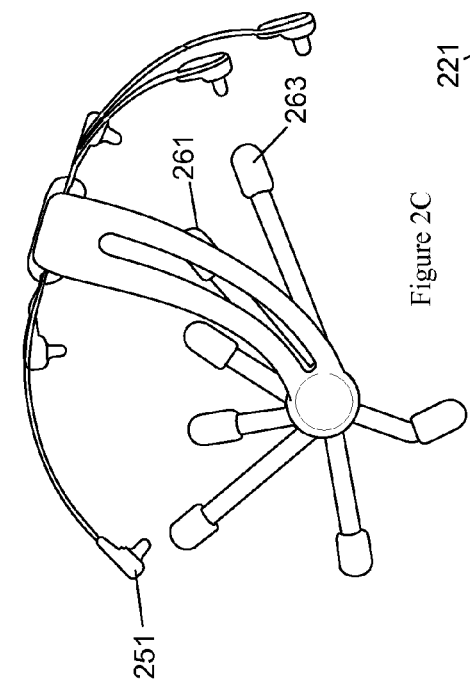

FIGS. 2A-2E illustrate a particular example of a neuro-response data collection mechanism. FIG. 2A shows a perspective view of a neuro-response data collection mechanism including multiple dry electrodes. According to some examples, the neuro-response data collection mechanism is a headset having point or teeth electrodes configured to contact the scalp through hair without the use of electro-conductive gels. In some examples, each electrode is individually amplified and isolated to enhance shielding and routability. In some examples, each electrode has an associated amplifier implemented using a flexible printed circuit. Signals may be routed to a controller/processor for immediate transmission to a data analyzer or stored for later analysis. A controller/processor may be used to synchronize neuro-response data with stimulus materials. The neuro-response data collection mechanism may also have receivers for receiving clock signals and processing neuro-response signals. The neuro-response data collection mechanisms may also have transmitters for transmitting clock signals and sending data to a remote entity such as a data analyzer.

FIGS. 2B-2E illustrate top, side, rear, and perspective views of the neuro-response data collection mechanism. The neuro-response data collection mechanism includes multiple electrodes including right side electrodes 261 and 263, left side electrodes 221 and 223, front electrodes 231 and 233, and rear electrode 251. It should be noted that specific electrode arrangement may vary from implementation to implementation. However, example techniques and mechanisms of the present disclosure avoid placing electrodes on the temporal region to prevent collection of signals generated based on muscle contractions. Avoiding contact with the temporal region also enhances comfort during sustained wear.

According to some examples, forces applied by electrodes 221 and 223 counterbalance forces applied by electrodes 261 and 263. In some examples, forces applied by electrodes 231 and 233 counterbalance forces applied by electrode 251. In some examples, the EEG dry electrodes operate to detect neurological activity with minimal interference from hair and without use of any electrically conductive gels. According to some examples, neuro-response data collection mechanism also includes EOG sensors such as sensors used to detect eye movements.

According to some examples, data acquisition using electrodes 221, 223, 231, 233, 251, 261, and 263 is synchronized with stimulus material presented to a user. Data acquisition can be synchronized with stimulus material presented by using a shared clock signal. The shared clock signal may originate from the stimulus material presentation mechanism, a headset, a cell tower, a satellite, etc. The data collection mechanism 201 also includes a transmitter and/or receiver to send collected neuro-response data to a data analysis system and to receive clock signals as needed. In some examples, a transceiver transmits all collected media such as video and/or audio, neuro-response, and sensor data to a data analyzer. In other examples, a transceiver transmits only interesting data provided by a filter. According to some examples, neuro-response data is correlated with timing information for stimulus material presented to a user.

In some examples, the transceiver can be connected to a computer system that then transmits data over a wide area network to a data analyzer. In other examples, the transceiver sends data over a wide area network to a data analyzer. Other components such as fMRI and MEG that are not yet portable but may become portable at some point may also be integrated into a headset.

It should be noted that some components of a neuro-response data collection mechanism have not been shown for clarity. For example, a battery may be required to power components such as amplifiers and transceivers. Similarly, a transceiver may include an antenna that is similarly not shown for clarity purposes. It should also be noted that some components are also optional. For example, filters or storage may not be required.

FIG. 3 illustrates examples of data models that can be used for storage of information associated with collection of neuro-response data. According to some examples, a dataset data model 301 includes a name 303 and/or identifier, client attributes 305, a subject pool 307, logistics information 309 such as the location, date, and stimulus material 311 identified using user entered information or video and audio detection.

In some examples, a subject attribute data model 315 includes a subject name 317 and/or identifier, contact information 321, and demographic attributes 319 that may be useful for review of neurological and neuro-physiological data. Some examples of pertinent demographic attributes include marriage status, employment status, occupation, household income, household size and composition, ethnicity, geographic location, sex, race. Other fields that may be included in data model 315 include shopping preferences, entertainment preferences, and financial preferences. Shopping preferences include favorite stores, shopping frequency, categories shopped, favorite brands. Entertainment preferences include network/cable/satellite access capabilities, favorite shows, favorite genres, and favorite actors. Financial preferences include favorite insurance companies, preferred investment practices, banking preferences, and favorite online financial instruments. A variety of subject attributes may be included in a subject attributes data model 315 and data models may be preset or custom generated to suit particular purposes.

Other data models may include a data collection data model 337. According to some examples, the data collection data model 337 includes recording attributes 339, equipment identifiers 341, modalities recorded 343, and data storage attributes 345. In some examples, equipment attributes 341 include an amplifier identifier and a sensor identifier.

Modalities recorded 343 may include modality specific attributes like EEG cap layout, active channels, sampling frequency, and filters used. EOG specific attributes include the number and type of sensors used, location of sensors applied, etc. Eye tracking specific attributes include the type of tracker used, data recording frequency, data being recorded, recording format, etc. According to some examples, data storage attributes 345 include file storage conventions (format, naming convention, dating convention), storage location, archival attributes, expiry attributes, etc.

A preset query data model 349 includes a query name 351 and/or identifier, an accessed data collection 353 such as data segments involved (models, databases/cubes, tables, etc.), access security attributes 355 included who has what type of access, and refresh attributes 357 such as the expiry of the query, refresh frequency, etc. Other fields such as push-pull preferences can also be included to identify an auto push reporting driver or a user driven report retrieval system.

FIG. 4 illustrates examples of queries that can be performed to obtain data associated with neuro-response data collection. According to some examples, queries are defined from general or customized scripting languages and constructs, visual mechanisms, a library of preset queries, diagnostic querying including drill-down diagnostics, and eliciting what if scenarios. According to some examples, subject attributes queries 415 may be configured to obtain data from a neuro-informatics repository using a location 417 or geographic information, session information 421 such as timing information for the data collected. Location information 423 may also be collected. In some examples, a neuro-response data collection mechanism includes GPS or other location detection mechanisms. Demographics attributes 419 include household income, household size and status, education level, age of kids, etc.

Other queries may retrieve stimulus material recorded based on shopping preferences of subject participants, countenance, physiological assessment, completion status. For example, a user may query for data associated with product categories, products shopped, shops frequented, subject eye correction status, color blindness, subject state, signal strength of measured responses, alpha frequency band ringers, muscle movement assessments, segments completed, etc.

Response assessment based queries 437 may include attention scores 439, emotion scores, 441, retention scores 443, and effectiveness scores 445. Such queries may obtain materials that elicited particular scores. Response measure profile based queries may use mean measure thresholds, variance measures, number of peaks detected, etc. Group response queries may include group statistics like mean, variance, kurtosis, p-value, etc., group size, and outlier assessment measures. Still other queries may involve testing attributes like test location, time period, test repetition count, test station, and test operator fields. A variety of types and combinations of types of queries can be used to efficiently extract data.

FIG. 5 illustrates examples of reports that can be generated. According to some examples, client assessment summary reports 501 include effectiveness measures 503, component assessment measures 505, and neuro-response data collection measures 507. Effectiveness assessment measures include composite assessment measure(s), industry/category/client specific placement (percentile, ranking, etc.), actionable grouping assessment such as removing material, modifying segments, or fine tuning specific elements, etc, and the evolution of the effectiveness profile over time. In some examples, component assessment reports include component assessment measures like attention, emotional engagement scores, percentile placement, ranking, etc. Component profile measures include time based evolution of the component measures and profile statistical assessments. According to some examples, reports include the number of times material is assessed, attributes of the multiple presentations used, evolution of the response assessment measures over the multiple presentations, and usage recommendations.

According to some examples, client cumulative reports 511 include media grouped reporting 513 of all stimulus assessed, campaign grouped reporting 515 of stimulus assessed, and time/location grouped reporting 517 of stimulus assessed. According to some examples, industry cumulative and syndicated reports 521 include aggregate assessment responses measures 523, top performer lists 525, bottom performer lists 527, outliers 529, and trend reporting 531. In some examples, tracking and reporting includes specific products, categories, companies, brands.

Figure 6:
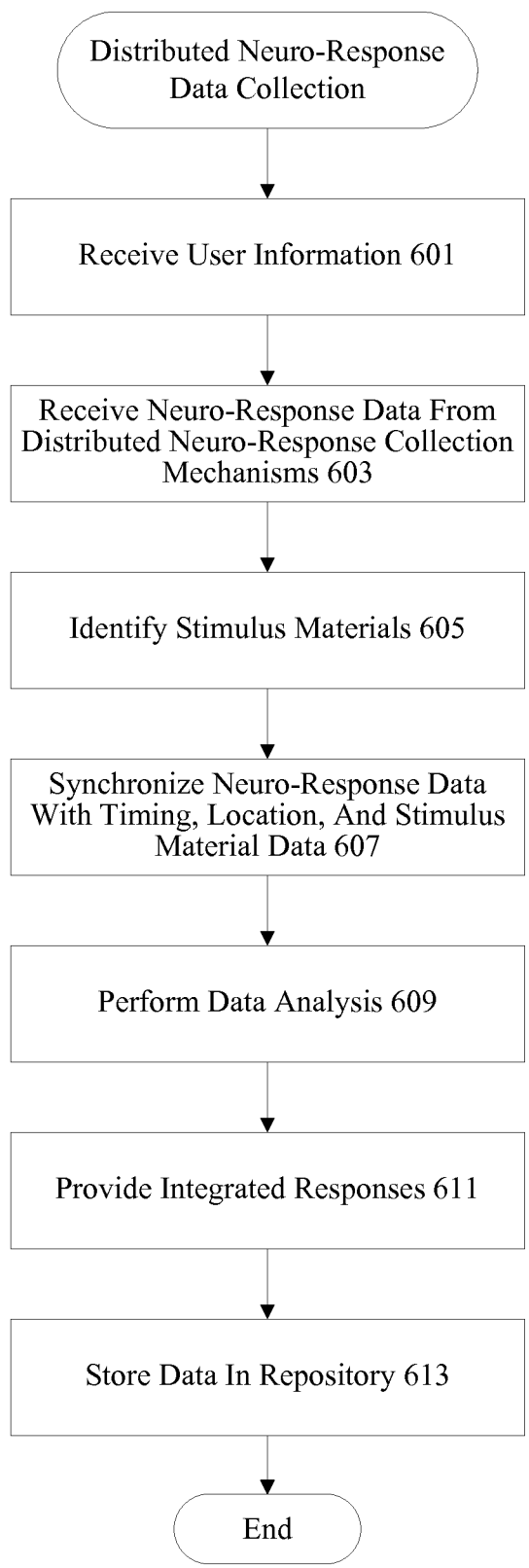
FIG. 6 illustrates one example of a technique for performing neuro-response data synchronization.

FIG. 6 illustrates one example of neuro-response data collection. At 601, user information is received from a subject provided with a neuro-response data collection mechanism. According to some examples, the subject sends data including age, gender, income, location, interest, ethnicity, etc. after being provided with an EEG headset including EEG electrodes.

At 603, neuro-response data is received from the subject neuro-response data collection mechanism. In some examples, EEG, EOG, pupillary dilation, facial emotion encoding data, video, images, audio, GPS data, etc., can all be transmitted from the subject to a neuro-response data analyzer. In some examples, only EEG data is transmitted. According to some examples, neuro-response and associated data is transmitted directly from an EEG cap wide area network interface to a data analyzer. In some examples, neuro-response and associated data is transmitted to a computer system that then performs compression and filtering of the data before transmitting the data to a data analyzer over a network.

According to some examples, data is also passed through a data cleanser to remove noise and artifacts that may make data more difficult to interpret. According to some examples, the data cleanser removes EEG electrical activity associated with blinking and other endogenous/exogenous artifacts. Data cleansing may be performed before or after data transmission to a data analyzer.

At 605, stimulus material is identified. According to some examples, stimulus material is identified based on user input or system data. Eye tracking movements can determine where user attention is focused at any given time. At 607, neuro-response data is synchronized with timing, location, and other stimulus material data. In some examples, neuro-response data is synchronized with a shared clock source. According to some examples, neuro-response data such as EEG and EOG data is tagged to indicate what the subject is viewing or listening to at a particular time.

At 609, data analysis is performed. Data analysis may include intra-modality response synthesis and cross-modality response synthesis to enhance effectiveness measures. It should be noted that in some particular instances, one type of synthesis may be performed without performing other types of synthesis. For example, cross-modality response synthesis may be performed with or without intra-modality synthesis.

A variety of mechanisms can be used to perform data analysis 609. In some examples, a stimulus attributes repository is accessed to obtain attributes and characteristics of the stimulus materials, along with purposes, intents, objectives, etc. In some examples, EEG response data is synthesized to provide an enhanced assessment of effectiveness. According to some examples, EEG measures electrical activity resulting from thousands of simultaneous neural processes associated with different portions of the brain. EEG data can be classified in various bands. According to some examples, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, example techniques and mechanisms of the present disclosure recognize that analyzing high gamma band (kappa-band: Above 60 Hz) measurements, in addition to theta, alpha, beta, and low gamma band measurements, enhances neurological attention, emotional engagement and retention component estimates. In some examples, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to some examples, high gamma waves (kappa-band) above 80 Hz (typically detectable with sub-cranial EEG and/or magnetoencephalography) can be used in inverse model-based enhancement of the frequency responses to the stimuli.

Some examples disclosed herein recognize that particular sub-bands within each frequency range have particular prominence during certain activities. A subset of the frequencies in a particular band is referred to herein as a sub-band. For example, a sub-band may include the 40-45 Hz range within the gamma band. In some examples, multiple sub-bands within the different bands are selected while remaining frequencies are band pass filtered. In some examples, multiple sub-band responses may be enhanced, while the remaining frequency responses may be attenuated.

An information theory based band-weighting model is used for adaptive extraction of selective dataset specific, subject specific, task specific bands to enhance the effectiveness measure. Adaptive extraction may be performed using fuzzy scaling. Stimuli can be presented and enhanced measurements determined multiple times to determine the variation profiles across multiple presentations. Determining various profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to some examples, the synchronous response may be determined for multiple subjects residing in separate locations or for multiple subjects residing in the same location.

Although a variety of synthesis mechanisms are described, it should be recognized that any number of mechanisms can be applied in sequence or in parallel with or without interaction between the mechanisms.

Although intra-modality synthesis mechanisms provide enhanced significance data, additional cross-modality synthesis mechanisms can also be applied. A variety of mechanisms such as EEG, Eye Tracking, GSR, EOG, and facial emotion encoding are connected to a cross-modality synthesis mechanism. Other mechanisms as well as variations and enhancements on existing mechanisms may also be included. According to some examples, data from a specific modality can be enhanced using data from one or more other modalities. In some examples, EEG typically makes frequency measurements in different bands like alpha, beta and gamma to provide estimates of significance. However, example techniques of the present disclosure recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to some examples, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to some examples, time corrected GSR measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to some examples, ERP measures are enhanced using EEG time-frequency measures (ERPSP) in response to the presentation of the marketing and entertainment stimuli. Specific portions are extracted and isolated to identify ERP, DERP and ERPSP analyses to perform. In some examples, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to some examples, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In some examples, specific EEG signatures of activity such as slow potential shifts and measures of coherence in time-frequency responses at the Frontal Eye Field (FEF) regions that preceded saccade-onset are measured to enhance the effectiveness of the saccadic activity data.

According to some examples, facial emotion encoding uses templates generated by measuring facial muscle positions and movements of individuals expressing various emotions prior to the testing session. These individual specific facial emotion encoding templates are matched with the individual responses to identify subject emotional response. In some examples, these facial emotion encoding measurements are enhanced by evaluating inter-hemispherical asymmetries in EEG responses in specific frequency bands and measuring frequency band interactions. Example techniques of the present disclosure recognize that not only are particular frequency bands significant in EEG responses, but particular frequency bands used for communication between particular areas of the brain are significant. Consequently, these EEG responses enhance the EMG, graphic and video based facial emotion identification.

Integrated responses are generated at 611. According to some examples, the data communication device transmits data to the response integration using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures. According to some examples, data is sent using a telecommunications, wireless, Internet, satellite, or any other communication mechanisms that is capable of conveying information from multiple subject locations for data integration and analysis. The mechanism may be integrated in a set top box, computer system, receiver, mobile device, etc.

In some examples, the data communication device sends data to the response integration system. According to some examples, the response integration system combines analyzed and enhanced responses to the stimulus material while using information about stimulus material attributes. In some examples, the response integration system also collects and integrates user behavioral and survey responses with the analyzed and enhanced response data to more effectively measure and track neuro-responses to stimulus materials. According to some examples, the response integration system obtains attributes such as requirements and purposes of the stimulus material presented.

Some of these requirements and purposes may be obtained from a variety of databases. According to some examples, the response integration system also includes mechanisms for the collection and storage of demographic, statistical and/or survey based responses to different entertainment, marketing, advertising and other audio/visual/tactile/olfactory material. If this information is stored externally, the response integration system can include a mechanism for the push and/or pull integration of the data, such as querying, extraction, recording, modification, and/or updating.

The response integration system can further include an adaptive learning component that refines user or group profiles and tracks variations in the neuro-response data collection system to particular stimuli or series of stimuli over time. This information can be made available for other purposes, such as use of the information for presentation attribute decision making. According to some examples, the response integration system builds and uses responses of users having similar profiles and demographics to provide integrated responses at 611. In some examples, stimulus and response data is stored in a repository at 613 for later retrieval and analysis.

Figure 7:
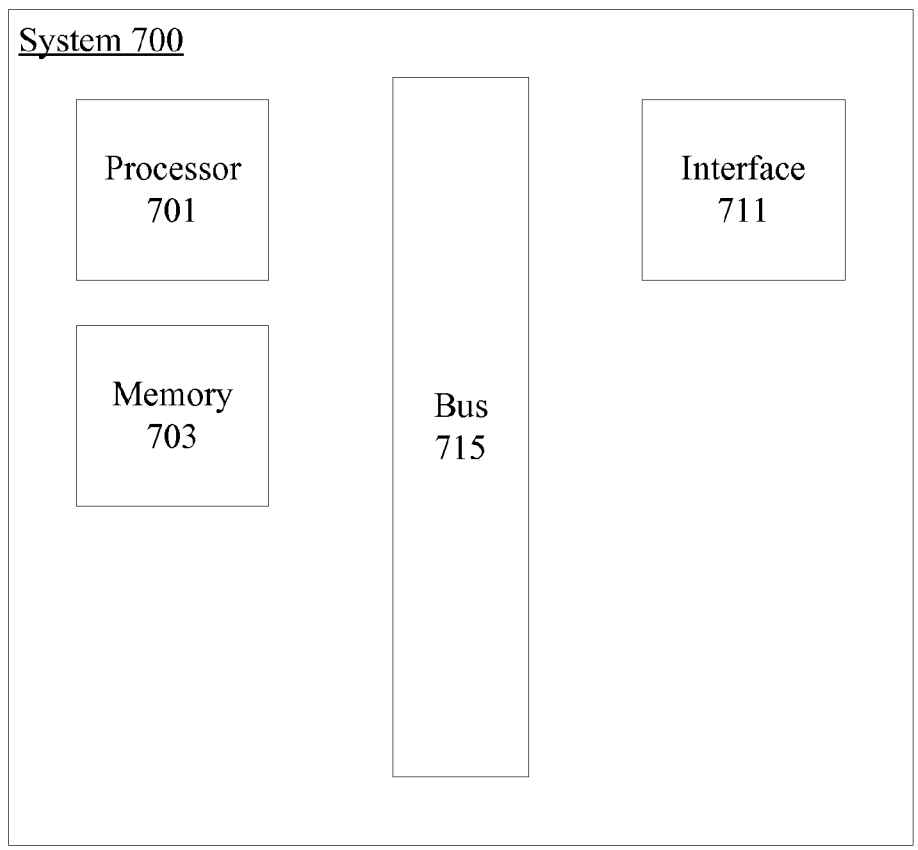
FIG. 7 provides one example of a system that can be used to implement one or more example mechanisms or processes disclosed herein.

According to some examples, at least some of the example mechanisms such as the data collection mechanisms, the intra-modality synthesis mechanisms, cross-modality synthesis mechanisms, etc. are implemented on multiple devices. However, it is also possible that the example mechanisms be implemented in hardware, firmware, and/or software in a single system. FIG. 7 provides one example of a system 700 that can be used to implement one or more mechanisms. For example, the system 700 shown in FIG. 7 may be used to implement a data analyzer.

The example system 700, which is suitable for implementing some examples disclosed herein, includes a processor 701, a memory 703, an interface 711, and a bus 715 (e.g., a PCI bus). When acting under the control of appropriate software or firmware, the processor 701 is responsible for such tasks such as pattern generation. Various specially configured devices can also be used in place of a processor 701 or in addition to processor 701. The complete implementation can also be done in custom hardware. The interface 711 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as data synthesis.

According to some examples, the system 700 uses memory 703 to store data, algorithms and program instructions. The program instructions may control the operation of an operating system and/or one or more applications, for example. The memory or memories may also be configured to store received data and process received data.

Because such information and program instructions may be employed to implement the systems/methods described herein, some examples employ tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing examples have been described in some detail for purposes of clarity of understanding, it will be apparent that certain changes and modifications may be practiced within the scope of the claims. Therefore, the present examples are to be considered as illustrative and not restrictive and the present disclosure is not to be limited to the details given herein, but may be modified within the scope and equivalents of the claims.

What is claimed is:

1. A system comprising:
 a headset to gather data including first neuro-response data and second neuro-response data from a user while the user is exposed to stimulus material, the headset including:
  a band;
  a first sensor extending from the band to be located on a first position on a head of the user when the user is wearing the headset, the first sensor to gather the first neuro-response data, the first neuro-response data including at least one of electroencephalographic data or magnetoencephalographic data;
  a second sensor extending from the band to be located on a second position on the head of the user when the user is wearing the headset, the second sensor to gather second neuro-response data, the second neuro-response data including at least one of electroencephalographic data or magnetoencephalographic data, wherein when coupled to the band, the first sensor and the second sensor are rotatably positionable relative to the band, wherein rotation of the first sensor from the first position to a third position on the head of the user rotates the second sensor relative to the band from the second position to a fourth position on the head of the user when the user is wearing the headset; and a processor programmed to:
synchronize the first neuro-response data, the second neuro-response data and the stimulus material to generate synchronized data; and
determine an effectiveness of a portion of the stimulus material based on the synchronized data.

2. The system of claim 1, wherein the headset further includes an identifier to identify the stimulus material.

3. The system of claim 1, wherein the first sensor and the second sensor are electrodes and the processor is programmed to process signals from active ones of the electrodes for analysis.

4. The system of claim 1, wherein the first sensor and the second sensor are electrodes and the processor is programmed to process signals from a subset of the plurality of electrodes for analysis that are active channels.

5. The system of claim 1, wherein the headset is a first headset, the data is first data, and the user is a first user, further including a second headset to gather second data from a second user while the second user is exposed to the stimulus material.

6. The system of claim 5, further including a receiver to receive the first data from the first user and the second data from the second user, the effectiveness based on the first data and the second data.

7. The system of claim 1, further including a third sensor to gather eye-tracking data, wherein the processor is programmed to analyze the eye-tracking data to determine a direction of the attention of the user.

8. The system of claim 1, wherein the headset further includes a first rotatable hub and the first sensor includes a first electrode coupled to the first hub at a first distance.

9. The system of claim 8, wherein the second sensor includes a second electrode coupled to the first hub at a second distance, the second distance different than the first distance.

10. The system of claim 9, wherein the headset further includes a second rotatable hub and a third electrode and a fourth electrode extend from the second hub.

11. The system of claim 1, further including a third sensor to gather facial data, the facial data including facial emotion encoding data.

12. The system of claim 11, wherein the third sensor includes a facial affect graphic and video analyzer.

13. The system of claim 11, wherein the headset further includes a recorder to record the stimulus material.

14. The system of claim 13, wherein the headset further includes a transmitter to transmit the recorded stimulus material and one or more of the first neuro-response data, the second neuro-response data, the facial data, the synchronized data, or the determined effectiveness to a remote processor.

15. The system of claim 11, wherein the processor is programmed to determine when the user is not paying attention to the stimulus material based on at least one of the first neuro-response data, the second neuro-response data, the facial data, or the synchronized data.

16. A method comprising:
collecting data with a headset worn by a user while the user is exposed to stimulus material, the data including (1) first neuro-response data gathered by a first sensor carried by a band, the first neuro-response data including at least one of electroencephalographic data or magnetoencephalographic data, and (2) second neuro-response data gathered by a second sensor carried by the band, the second neuro-response data including at least one of electroencephalographic data or magnetoencephalographic data, wherein when coupled to the band, the first sensor and the second sensor are rotatably positionable relative to the band, wherein rotation of the first sensor from a first position on a head of the user to a second position on the head of the user rotates the second sensor relative to the band from a third position on the head of the user to a fourth position on the head of the user;
generating synchronized data with a processor by synchronizing the first neuro-response data, the second neuro-response data and the stimulus material; and
determining an effectiveness of a portion of the stimulus material based on the synchronized data.

17. The method of claim 16, wherein the headset is a first headset, the data is first data, and the user is a first user, further including collecting second data with a second headset worn by a second user while the second user is exposed to the stimulus material.

18. The method of claim 17, further including synchronizing the synchronized data from the first user and the second data from the second user to determine a synchronized measure of effectiveness.

19. The method of claim 17, wherein the first user and the second user are in different geographical locations when exposed to the stimulus material.

20. The method of claim 19, wherein the different geographical locations are different buildings.

21. The method of claim 16 further including analyzing eye-tracking data gathered by a third sensor to determine a direction of attention of the user.

22. The method of claim 16 further including receiving, via a clock signal receiver on the headset, a clock signal representing timing information of the stimulus material, wherein the synchronized data is generated by the processor based on the timing information.

23. The method of claim 22, wherein the clock signal receiver is a cell tower signal receiver or a satellite signal receiver, and wherein receiving the clock signal includes receiving the clock signal from a cell tower or a satellite.

24. The method of claim 22, wherein receiving the clock signal includes receiving the clock signal from a stimulus presentation device that presents the stimulus material to the user.

25. The method of claim 16, wherein the data further includes facial data gathered by a third sensor, the facial data including facial emotion encoding data.

* * * * *